(12) United States Patent
Hay et al.

(10) Patent No.: US 12,667,118 B2
(45) Date of Patent: Jun. 30, 2026

(54) COMPOSITIONS COMPRISING ALGAE AND METHODS OF USING SAME FOR INCREASING ANIMAL PRODUCT PRODUCTION

(71) Applicant: BLUE OCEAN BARNS, Kailua-Kona, HI (US)

(72) Inventors: Vivienne Hay, Redwood City, CA (US); Matthew Rothe, Stanford, CA (US); Joan Salwen, Redwood City, CA (US); Michael Bracco, Oakland, CA (US); Steve Krawczyk, Kailua-Kona, HI (US); Gal Dishon, San Diego, CA (US)

(73) Assignee: BLUE OCEAN BARNS, Kailua-Kona, HI (US)

( * ) Notice: Subject to any disclaimer, the term of this patent is extended or adjusted under 35 U.S.C. 154(b) by 596 days.

(21) Appl. No.: 17/917,732

(22) PCT Filed: Apr. 12, 2021

(86) PCT No.: PCT/IB2021/053022
§ 371 (c)(1),
(2) Date: Oct. 7, 2022

(87) PCT Pub. No.: WO2021/205420
PCT Pub. Date: Oct. 14, 2021

(65) Prior Publication Data
US 2023/0165274 A1 Jun. 1, 2023

Related U.S. Application Data

(63) Continuation-in-part of application No. 17/102,287, filed on Nov. 23, 2020, now Pat. No. Plant 34,607.
(Continued)

(51) Int. Cl.
*A23K 10/30* (2016.01)
*A01G 33/00* (2006.01)
(Continued)

(52) U.S. Cl.
CPC .............. *A23K 10/30* (2016.05); *A01G 33/00* (2013.01); *A01H 13/00* (2013.01); *A23K 20/105* (2016.05); *A23K 50/10* (2016.05)

(58) Field of Classification Search
CPC ...... A23K 10/30; A23K 20/105; A23K 50/10; A23K 10/10; A23K 10/12; A23K 10/16;
(Continued)

(56) References Cited

U.S. PATENT DOCUMENTS

PP21,091 P3    6/2010   Nonomura
PP23,858 P3    8/2013   Biel
(Continued)

FOREIGN PATENT DOCUMENTS

WO    2010039030 A1    4/2010
WO    2015109362 A2    7/2015
WO    2018018062 A1    2/2018

OTHER PUBLICATIONS

Nunes, Nuno, S. Valente, SÃ³nia Ferraz, Maria Carmo Barreto, and MAA Pinheiro De Carvalho. "Nutraceutical potential of Asparagopsis taxiformis (Delile) Trevisan extracts and assessment of a downstream purification strategy." 2018, Retrieved from the IDS, Heliyon 4, No. 11. (Year: 2018).*
(Continued)

*Primary Examiner* — Nikki H. Dees
*Assistant Examiner* — Joseph Cullen Merchlinsky
(74) *Attorney, Agent, or Firm* — BCF LLP

(57) ABSTRACT

The present technology generally relates to a method for determining inclusion rates of red algae into livestock feed and livestock supplements.

12 Claims, 16 Drawing Sheets

Related U.S. Application Data

(60) Provisional application No. 63/124,383, filed on Dec. 11, 2020, provisional application No. 63/117,390, filed on Nov. 23, 2020, provisional application No. 63/008,373, filed on Apr. 10, 2020, provisional application No. 63/008,356, filed on Apr. 10, 2020, provisional application No. 63/008,348, filed on Apr. 10, 2020, provisional application No. 63/008,352, filed on Apr. 10, 2020, provisional application No. 63/008,357, filed on Apr. 10, 2020, provisional application No. 63/008,363, filed on Apr. 10, 2020.

(51) Int. Cl.
| | |
|---|---|
| *A01H 13/00* | (2006.01) |
| *A23K 20/105* | (2016.01) |
| *A23K 50/10* | (2016.01) |

(58) Field of Classification Search
CPC ........ A23K 50/75; A23K 50/80; A01G 33/00; A01H 13/00
See application file for complete search history.

(56) References Cited

U.S. PATENT DOCUMENTS

| | | | |
|---|---|---|---|
| 2012/0238683 A1 | 9/2012 | Burba | |
| 2016/0339067 A1* | 11/2016 | Machado | A23K 50/10 |
| 2018/0271922 A1* | 9/2018 | Machado | A23K 50/10 |

OTHER PUBLICATIONS

Machado, Lorenna, Marie Magnusson, Nicholas A. Paul, Robert Kinley, Rocky de Nys, and Nigel Tomkins.2016"Identification of bioactives from the red seaweed *Asparagopsis taxiformis* that promote antimethanogenic activity in vitro.", Retrieved from the Internet, Journal of Applied Phycology 28: 3117-3126. (Year: 2016).*

Machado, Lorenna, Marie Magnusson, Nicholas A. Paul, Robert Kinley, Rocky de Nys, and Nigel Tomkins. "Dose-response effects of *Asparagopsis taxiformis* and *Oedogonium* sp. on in vitro fermentation and methane production.", 2016, Retrieved from the Internet, Journal of Applied Phycology 28: 1443-1452. (Year: 2016).*

Bonin, Denise R., and Michael W. Hawkes. "Systematics and life histories of New Zealand Bonnemaisoniaceae (Bonnemaisoniales, Rhodophyta): I. The genus *Asparagopsis*." 1987, Retrieved from the Internet, New Zealand Journal of Botany 25, No. 4 : 577-590. (Year: 1987).*

Nunes et al., Nutraceutical potential of Asparagopsis taxiformis (delile) Trevisan extracts and assessment of a downstream purification strategy, Nov. 2018, Heliyon vol. 4, Issue 11.

Wikipedia, Tetrasporaphyte, Jun. 12, 2018, https://en.wikipedia.org/w/index.php?title=Tetrasporaphyte&oldid=845492494.

International Search Report and Written Opinion issued in corresponding International application No. PCT/IB2021/053022 on Aug. 17, 2021.

Vucko, M.J. et al., The effects of processing on the in vitro antimethanogenic capacity and concentration of secondary metabolites of Asparagopsis taxiformis, Journal of Applied Phycology, Kluwer, Dordrecht, NL, vol. 29, No. 3, Nov. 15, 2016.

Supplementary European Search Report issued in co-pending European application No. 21785593.1 on Apr. 4, 2024.

McConnell, O. et al., Halogen Chemistry of the Red Alga *Asparagopsis*, Phytochemistry, 1977, vol. 16, pp. 367-374.

Nunes, N. et al., Nutraceutical potential of Asparagopsis taxiformis (Delile) Trevisan extracts and assessment of a downstream purification strategy, Heliyon 4, 2018.

Wikipedia, Soxhlet extractor, https://en.wikipedia.org/w/index.php?title=Soxhlet_extractor&oldid=1280701505, Accessed Sep. 14, 2025.

Agency for Toxic Substances and Disease Registry, Toxicological Profile for Bromoform and Dibromochloromethane, Table 4-2 Physical and Chemical Properties of Bromoform and Dibromochloromethane, Aug. 2005.

Vucko, M.J. et al., The effects of precessing on the in vitro antimethanogenic capacity and concentration of secondary metabolites of Asparagopsis taxiformis, J. Appl Phycol, Nov. 2016.

Magnusson et al., Using oil immersion to deliver a naturally-derived, stable bromoform product from the red seaweed Asparagopsis taxiformis, Elsevier, Algal Research 51: 1-7, Sep. 10, 2020.

Turland, N. J. et al., International Code of Nomenclature for algae, fungi and plants, 2018, https://www.iapt-taxon.org/nomen/main.php.

Mata et al., Effects of hydrogen peroxide in the content of major volatile halogenated compounds in the red alga Asparagopsis taxiformis (Bonnemaisoniaceae), J. Appl Phycol (2011) 23:827-832.

Mata, L., Carbon/Nutrient balance in relation to biomass production and halogenated compound content in the red alga Asparagopsis Taxeformis (Bonnemaisoniaceae), J. Phycol. 48. 248-253 (2012).

* cited by examiner

COMPOSITIONS COMPRISING ALGAE AND METHODS OF USING SAME FOR INCREASING ANIMAL PRODUCT PRODUCTION

CROSS-REFERENCE TO RELATED APPLICATIONS

This application is a national phase filing under 35 U.S.C. 371 of International Application No. PCT/IB2021/053022, filed on Apr. 12, 2021, which claims the benefit of and priority to U.S. provisional patent application No. 63/008,348, filed on Apr. 10, 2020; U.S. provisional patent application No. 63/008,352, filed on Apr. 10, 2020; U.S. provisional patent application No. 63/008,357, filed on Apr. 10, 2020; U.S. provisional patent application No. 63/008,356, filed on Apr. 10, 2020; U.S. provisional patent application No. 63/008,363, filed on Apr. 10, 2020; U.S. provisional patent application No. 63/008,373, filed on Apr. 10, 2020; U.S. Plant patent application Ser. No. 17/102,287, filed on Nov. 23, 2020; and U.S. provisional patent application No. 63/117,390, filed on Nov. 23, 2020; and U.S. provisional patent application No. 63/124,383, filed on Dec. 11, 2020, the content of all of which is herein incorporated in their entirety by reference.

FIELD OF TECHNOLOGY

The present technology generally relates to algae-derived biomass and to compositions comprising same. The present technology also generally relates to use of such algae-derived biomass and compositions comprising same in methods for feeding animals, in methods for increasing animal product production; and in methods of decreasing methane emission from animals.

BACKGROUND

Methanogenesis (i.e., the production of methane by ruminant animals) is a major contributor to global greenhouse gas emissions. Scientific literature has demonstrated reductions in methane ($CH_4$) production of beef cattle and dairy cows when halogenated compounds are fed as part of the diet. See for example Roque et al., 2020: "Some haloalkanes are structural analogs of $CH_4$ and therefore competitively inhibit the methyl transfer reactions that are necessary in $CH_4$ biosynthesis. The $CH_4$ analogues include bromochloromethane (BCM), bromoform and chloroform and have been proven to be the most effective feed additives for reducing $CH_4$ production". There are two potential sources for halogenated compounds: artificial synthesis and natural production. Naturally synthesized bromoform, administered via supplementation of *Asparagopsis* spp. was found more effective than synthetic methane analogs (Machado et. al. 2018). Supplementation with gametophytes of *Asparagopsis taxiformis* comprising 7.8 mg/g of bromoform by dry weight has been found to mitigate an 80% reduction of methane gas production over a 147-day period in steers fed a 0.5% seaweed supplemented low forage total mixed ration (LF-TMR) (Roque, 2020).

Despite its efficacy, the potential of *Asparagopsis taxiformis* (AT) as a feed additive to inhibit methanogenesis in ruminant animals is constrained by several factors. These include its unpleasant odor, high iodine content, epiphytic nature, and the lack of capacity, especially in male AT specimens, to synthesize material concentrations of the halogenated compounds.

CSIRO, Meat and Livestock Australia, and James Cook University are also the holders of U.S. Pat. No. 9,980,995: Method for reducing total gas production and or methane production in a ruminant animal, incorporated herein by reference. This patent describes the administration of an effective amount of red marine macroalgae as a feed supplement, with the result being a reduction in methane production. The red macroalgae form of the species, *Asparagopsis taxiformis*, is specifically identified as one lifestage morphotype of the species effective in this method. This patent also mentions the filamentous tetrasporophyte lifestage of *Asparagopsis*.

US Patent Application 2019/0174793, Growth performance improvements in pasture and feedlot systems, incorporated herein by reference, discloses a method for improving the growth performance of a livestock animal in various farming systems, including providing a red marine macroalgae to the farming systems to enable consumption of the red marine macroalgae.

US Patent Application 2019/0174793 describes a formulation such that the animal is provided with of red marine macroalgae per day for animals maintained at pasture and states that amounts to about 1-5% of algae on a dry matter basis or 1-3% on an organic matter basis per day. US Patent Application 2019/0174793 also discloses providing an animal with about 200-600 g/day of algae for animals on a finishing diet in feedlots. In one example, this application discloses the filamentous tetrasporophyte lifestage of *Asparagopsis* as a potential feedstock for a feed pre-mix.

This present technology overcomes at least some of those challenges observed with the drawbacks observed in the field.

BRIEF DESCRIPTION OF DRAWINGS

The accompanying drawings, which are incorporated herein and form a part of the specification, illustrate the present disclosure and, together with the description, further serve to explain the principles thereof and to enable a person skilled in the pertinent art to make and use the same.

3

Figure 8:
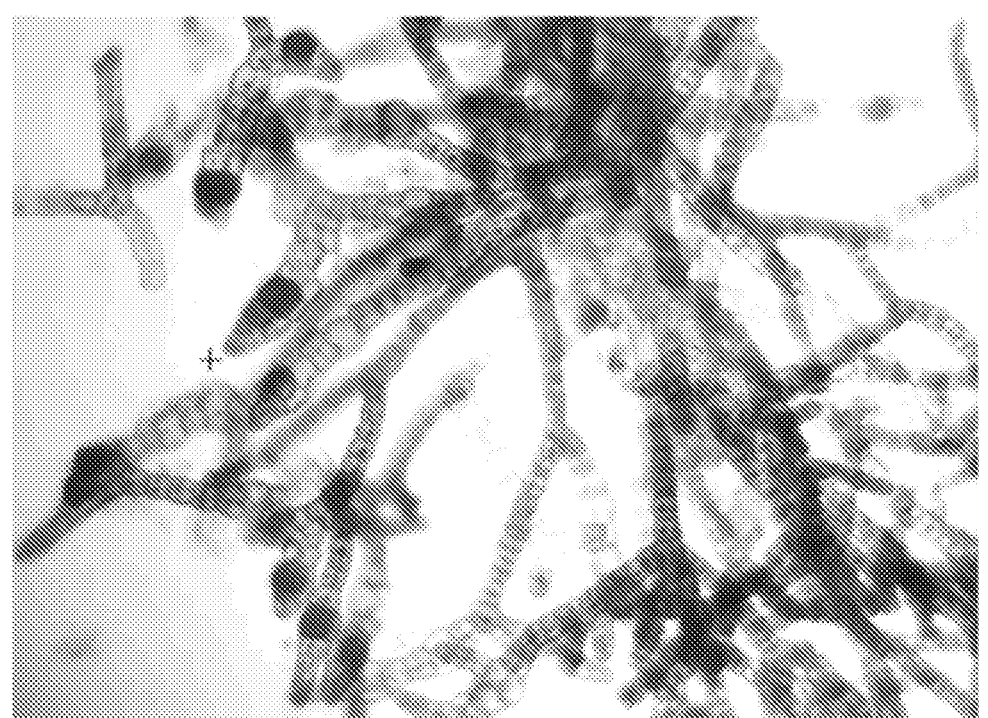

FIG. 8 is a photomicrograph of tetrasporophytes creating undesired spores. Spores detract energy from growth and bromoform synthesis.

Figure 9:

FIG. 9 is a photo of wild tetrasporophytes used as starting material for the breeding and cultivation program.

Figure 10:
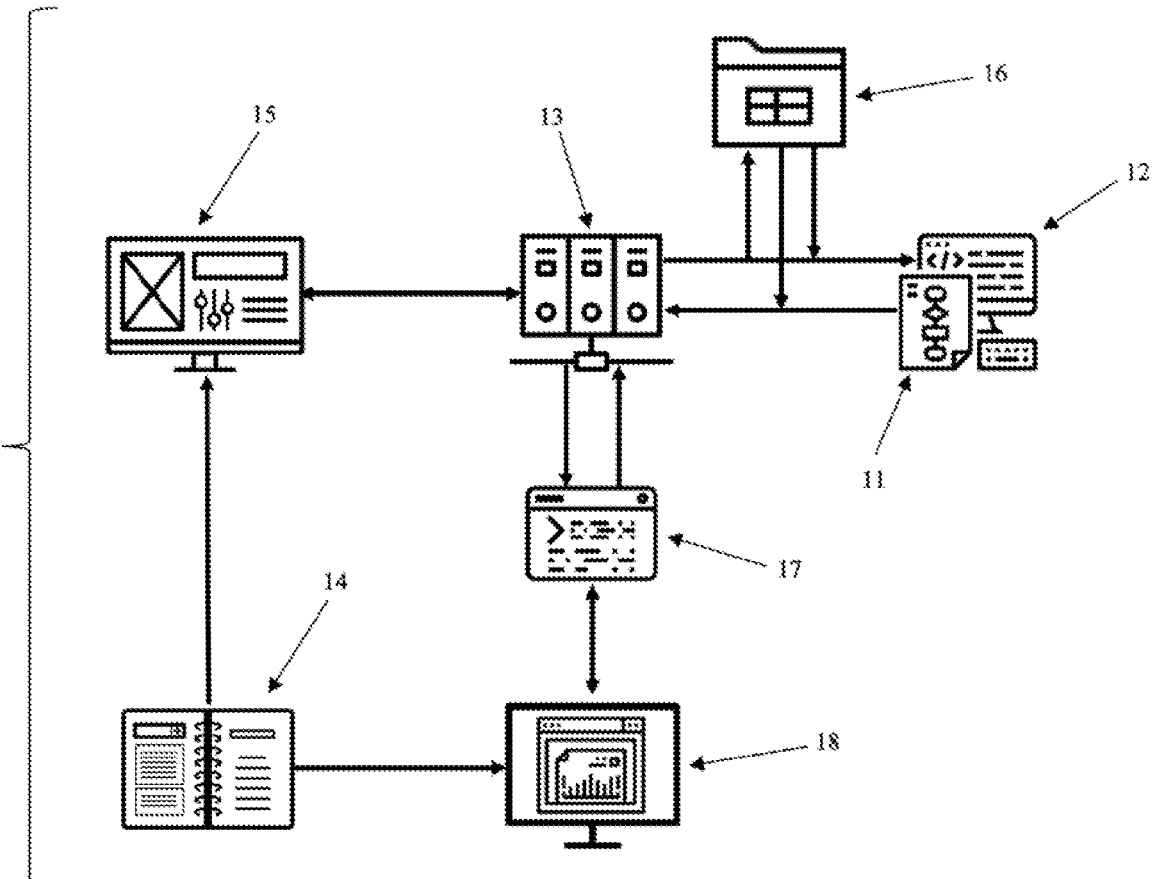

FIG. 10 depicts a graph illustrating a system that calculates precise inclusion rates of red algae in livestock feed and supplements according to one embodiment of the present technology.

Figure 11:
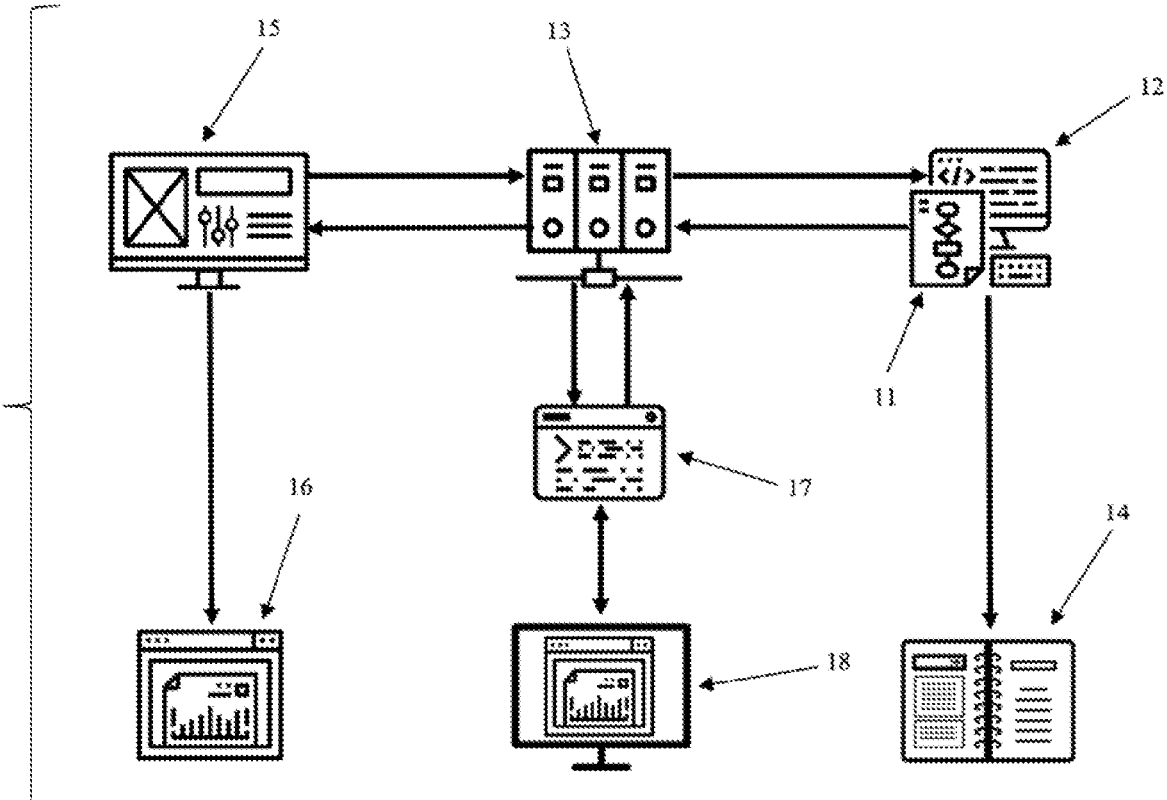

FIG. 11 depicts a graph illustrating a system in which biological methods are used to synthesize and encapsulate bromoform according to one embodiment of the present technology.

Figure 12:
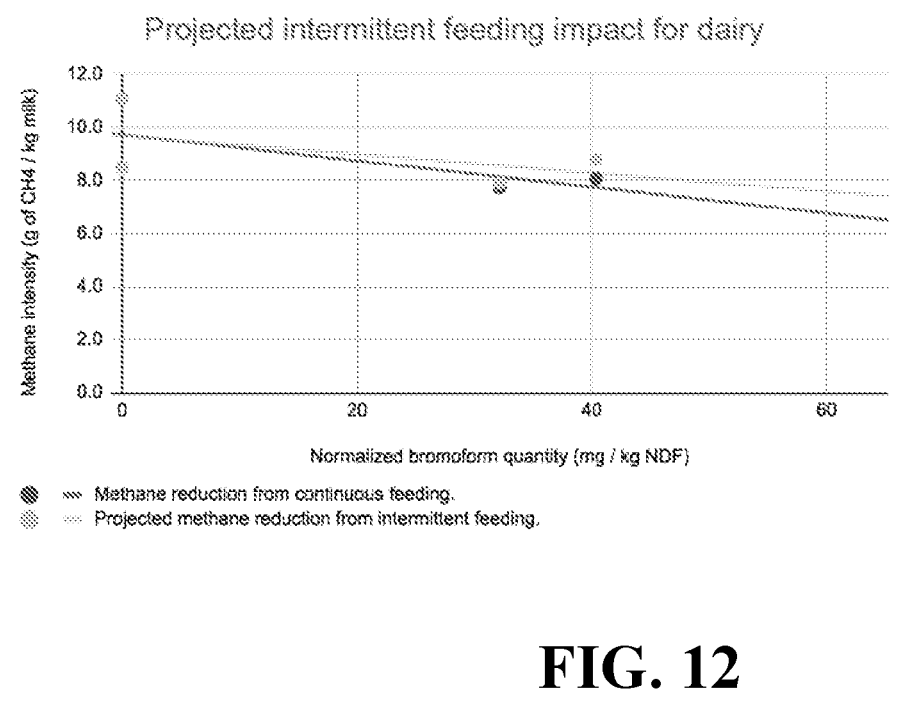

FIG. 12 depicts a graph showing projected intermittent feeding impact for dairy.

Figure 13:
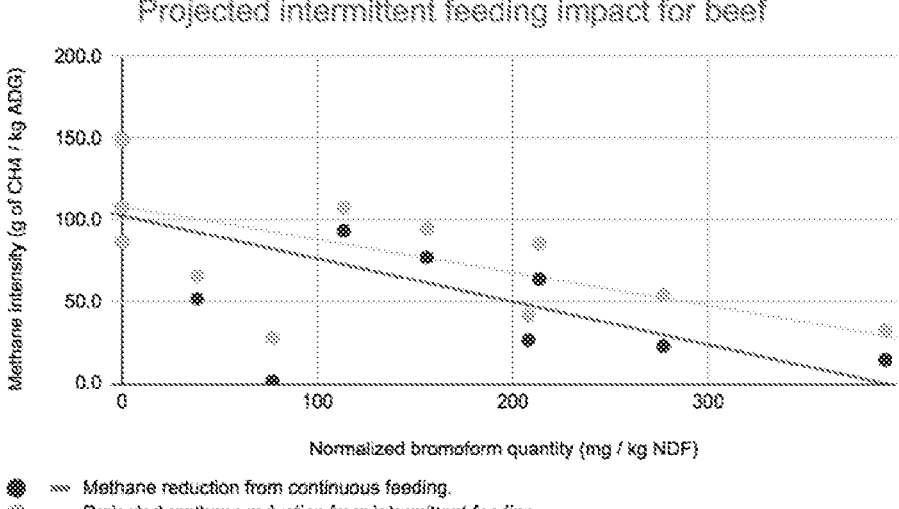

FIG. 13 depicts a graph showing projected intermittent feeding impact on beef.

SUMMARY OF TECHNOLOGY

The present technology seeks to address one or more of the above-mentioned problems or limitations. The following description of the embodiments of the technology is not intended to limit the technology to these embodiments, but rather to enable any person skilled in the art to make and use this technology.

In some aspects, the present technology relates to a biomass derived from *Asparagopsis taxiformis*, the biomass comprising a ratio of halogenated metabolite to iodine that is equal to or less than about 700:1. In some aspects, the present technology relates to a biomass derived from *Asparagopsis taxiformis*, the biomass comprising a ratio of halogenated metabolite to iodine that is between about 5:1 and about 700:1. In some aspects, the present technology relates to a biomass derived from *Asparagopsis taxiformis*, the biomass comprising a ratio of halogenated metabolite to iodine that is equal or greater than about 700:1. In some instances, the *Asparagopsis taxiformis* is *Asparagopsis taxiformis* tetrasporopgyte. In some instances, the halogenated metabolite is selected from any one of structures 1 to 78 of FIG. 1 or any combination thereof.

In some aspects, the present technology relates to a method for cultivating the biomass of as defined herein, the method comprising: i) collecting a parent *Asparagopsis taxiformis* plant; ii) manipulating the plant of i) to obtain filaments of *Asparagopsis* that are substantially free of contaminants; and selecting for *Asparagopsis taxiformis* aragopsis that exhibit enlarged gland cells.

In some aspects, the present technology relates to a method for reducing methane production in a ruminant, the method comprising administering between about 10 g and about 60 g per day of the biomass as described herein to the ruminant.

In some aspects, the present technology relates to a method for reducing methane production in a ruminant, the method comprising administering between about 10 g and about 30 g per day of the biomass as defined herein to the ruminant.

In some aspects, the present technology relates to a method for reducing methane production in a ruminant, the method comprising administering between about 5 g and about 25 g per day of the biomass as defined herein to the ruminant.

In some aspects, the present technology relates to a kit comprising an algal feed supplement comprising: at least about 20% of neutral dietary fiber (NDF) by dry weight of the algal feed supplement; at least about 16% protein by dry weight of the algal feed supplement; less than about 3000 ppm iodine by dry weight of the algal feed supplement; and at least about 2.5% of a halogenated metabolite by dry weight of the algal feed supplement.

DETAILED DESCRIPTION

The present technology is explained in greater detail below. This description is not intended to be a detailed catalog of all the different ways in which the technology may be implemented, or all the features that may be added to the instant technology. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which variations and additions do not depart from the present technology. Hence, the following description is intended to illustrate some particular embodiments of the technology, and not to exhaustively specify all permutations, combinations and variations thereof.

As used herein, the singular form "a", "an" and "the" include plural referents unless the context clearly dictates otherwise.

The recitation herein of numerical ranges by endpoints is intended to include all numbers subsumed within that range (e.g., a recitation of 1 to 5 includes 1, 1.5, 2, 2.75, 3, 3.80, 4, 4.32, and 5).

The term "about" is used herein explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. For example, the term "about" in the context of a given value or range refers to a value or range that is within 20%, preferably within 15%, more preferably within 10%, more preferably within 9%, more preferably within 8%, more preferably within 7%, more preferably within 6%, and more preferably within 5% of the given value or range.

The expression "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

When a quantifier such as "less than", "more than", or "greater than" modifies a comma delimited list of numbers or quantities, or ratios, such as "1, 2.5, 3, . . . " or "one, two, three . . . " the intention is that the quantifier applies to every member of the list. For example, "alpha is greater than about 1, 2, or 3, or 4" means "alpha is greater than about 1, or, alpha is greater than about 2 or alpha is greater than about 3."

It is only the female *Asparagopsis taxiformis* varieties that synthesize more than nominal amounts of bromoform, meaning that fifty (50%) percent of biomass is not meaningly contributing to the overall production efficiency. With the present technology, not only is one hundred (100%) percent of the biomass synthesizing bromoform, thereby almost doubling production efficiency, but the biomass of the present technology itself accumulates higher levels of bromoform than previously attainable with female gametophytes. Further benefits of the present technology include reducing odor, reducing iodine content and rejecting epiphytes, which is beneficial to cost-effective mass production of a high-quality additive. The *Asparagopsis taxiformis* variety of the present technology is anatomically distinguished from the parent plant in a number of ways and was accomplished by a vegetative breeding program to increase bromoform concentration under novel cultivation environments. Tests were initially carried out to test typical wild *Asparagopsis taxiformis* gametophytes for bromoform and it was found a typical sample comprised 6.63 mg/g of bromoform for freeze dried material, matching closely the value reported by Machado. Next, wild *Asparagopsis taxiformis* tetrasporophytes was harvested, as shown in FIG. 9 and it was found to comprised only 1.1 mg/g of bromoform. Even with the increased ease of cultivation, this level of bromoform would make commercial supplementation of cattle costly. Surprisingly, the present investigators discovered that under controlled conditions, a distinct variety and cultivation conditions that provided for *Asparagopsis taxiformis* tetrasporophytes typically comprising 9.4 mg/g or more bromoform could be developed. For example, using these methods samples of *Asparagopsis taxiformis* tetrasporophytes have been cultivated with 18.5 mg/g $HCBr_3$ have been obtained. Likewise, other *Asparagopsis taxiformis* tetrasporophytes samples have shown iodine levels of 0.142 mg/g. This sample had an $HCBr_3$ to I ratio of 83.8 w/w of dried material.

Figure 2:
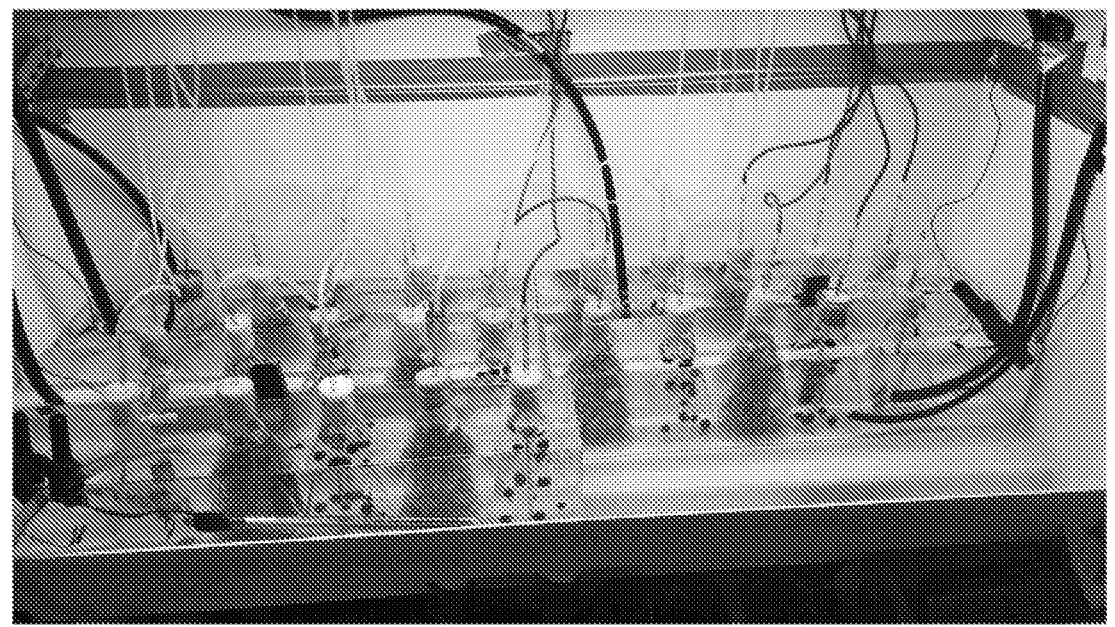
FIG. 2 shows the growth of tetrasporophyte material in the nursery as the "filamentous" form (uniform red material in the Erlenmeyer flasks, and the "puffball" form as the darker red floating spheres.
Figure 3:
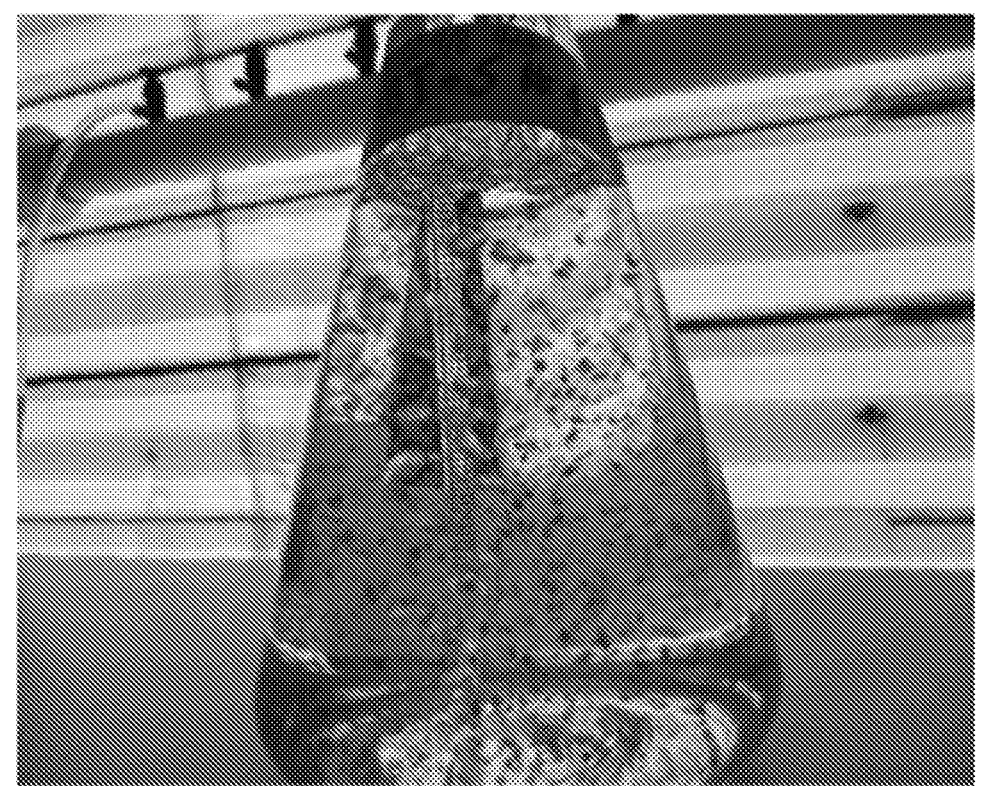
FIG. 3 shows a closeup of the non-filamentous tetrasporophyte form.
Figure 4:
FIG. 4 shows another closeup of the non-filamentous tetrasporophyte form.

While under typical cultivation conditions *Asparagopsis* spp. tetrasporophytes quickly mature to a filamentous form that has been previously studied as a feed supplement, under our conditions, the tetrasporophytes maintain a non-filamentous appearance, grow rapidly, exhibit high bromoform concentrations, have low iodine concentration/bromoform concentration ratios and can be kept in these stages in bioreactors for indefinite times. These morphotypes can be described as, "puff ball" forms. Both the filamentous and non-filamentous puffball forms are shown in FIGS. 2-4.

Moreover, the supplement comprising the tetrasporophyte variety grown under the herein described conditions can be supplemented without the necessity of adding molasses to the biomass that is typically needed to increase palatability and prevent feed refusal. In another aspect, the feed supplement compositions of the present technology do not comprise sweeteners such as, but not limited to, molasses, high fructose corn syrup, sucrose, fructose, xylitol, sorbitol, or other alcohol sugar appetants.

In still another aspect, the feed supplement compositions of the present technology may be used to supplement animals at a rate of less than 10 g/day, or 7.5 g/day, or 5 g/day of the algal biomass described here for animals grazing on a pasture. In yet another aspect, the feed supplement compositions of the present technology may be used to supplement feedlot animals on finishing diets at a daily supplementation rate of less than 200 g/day, less about 150 g/day, less than 100 g/day, or 50 g/day of the algal biomass described here for animals on finishing diets. In general, animals will have different supplementation rates depending on whether they are being raised for dairy or meat, are grazed solely on pasture, solely on grain, or on transition diets. Particularly, the algorithms and supplementation rates and methods described herein will take into account the amount of neutral dietary fiber (NDF, or sometimes referred to as aNDF).

Figure 6:
FIG. 6 shows naturally occurring gametophytes (the parent plant) and some anatomical differences between tetrasporophytes and gametophytes, for example in terms of the size and shape of the plants.

Additionally, the present investigators discovered how to induce the growth and indefinite maintenance of "puffball" forms of the tetrasporophyte that appear to be microscopic oligocellular forms which are very morphologically and chemotypically distinct from the gametophyte macroalgal stage shown in FIG. 6. In particular, the present investigators discovered that certain of these tetrasporophyte varieties in particular morphotypes are very well suited for use as feed supplements as a source of halogenated compounds to inhibit methanogenesis, promote growth of animals (e.g., ruminant animals) as well as increase the quality of products derived therefrom.

Figure 7:
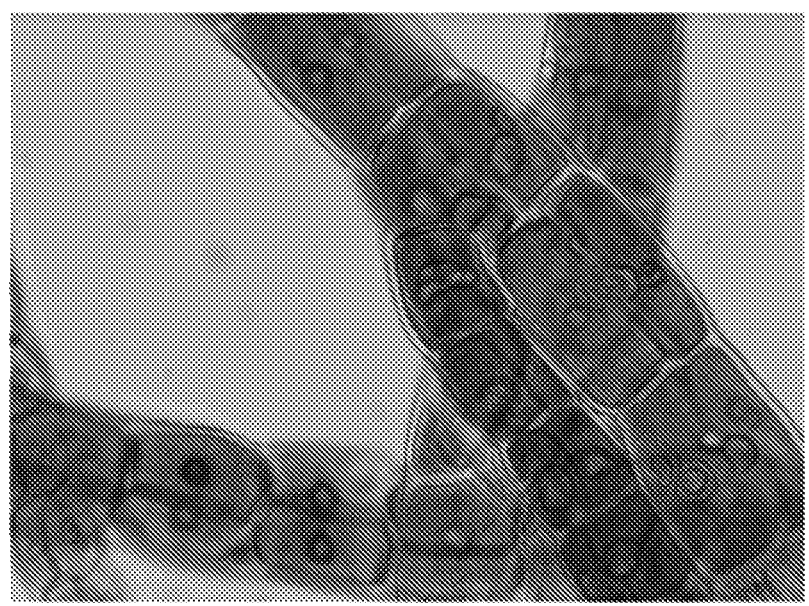
FIG. 7 shows a photomicrograph of tetrasporophyte material growing in the laboratory. Note the unusually large gland cells (the orange/black dots). The gland cells are what contains the active ingredient (bromoform). Large gland cells indicate an unusually high concentration of bromoform.

In one embodiment, the present technology thus relates to a *Asparagopsis taxiformis* that is created through the aforementioned collection, manipulation, dissection and selection process. The resulting plant is a small red alga comprising microscopic branched chains of cells shown in FIG. 7. Unlike the gametophyte form, where cells have differentiated functions (holdfast, stem, blades etc.), the cells in the tetrasporophyte are not highly differentiated. Instead, each cluster of four cells is roughly equivalent and these clusters string together into long chains. The color ranges from pale pink to red to dark cherry. Each branch contains gland cells where the bromoform is stored. These gland cells are a dark red to brown in color, with deeper color indicating higher bromoform concentration. The plant is not rooted, but rather free-floating in water. It obtains all its organic and inorganic nutrients from the water and can live in this state indefinitely.

In one embodiment, this variety is anatomically distinguished from others by stasis in the third phase, the tetrasporophyte phase. Wild AT typically follows a progression through three life stages (gametophyte, carposporophyte and tetrasporophyte). The present variety is static in the tetrasporophyte phase. This is particularly beneficial because one hundred (100%) percent of tetrasporophytes create high levels of bromoform, in contrast to just fifty (50%) percent of gametophytes synthesize meaningful amounts of bromoform. In addition, since the present tetrasporophytes are static in phase they are not producing spores, unlike the tetrasporophyte form shown in FIG. 8. This means they can devote all of their energy to growth, which is correlated with even higher bromoform concentrations.

Furthermore, in one embodiment, the present variety is specific even within the tetrasporophyte class. While tetrasporophytes, left to their own devices, devolve from "puffballs" into a filamentous form, the present tetrasporophytes can be maintained in the "puffball" phase. This is advantageous because the "puffball" form grows faster than the filamentous form. Again, this may be correlated with higher bromoform concentrations.

The variety of the present technology is not limited to the "puffballs" form but also encompasses the larger, "cotton ball" form and the longer "filamentous" chains.

Given these anatomical differences, the composition of the present variety is materially different to the mother variety. In particular, it has a much higher bromoform to iodine ratio. Without wishing to be bound to a particular theory, it is believed that the lower iodine levels may, in part, be due to high rates of bromoform synthesis and storage displacing iodine in gland cells (where bromoform is stored), as outlined in Table 1 below:

TABLE 1

Comparison of Bromoform and Iodine content in Gametophyte and Tetrasporophyte

| Sample | Type of material | Iodine (ppm) | Average bromoform (μg/g) | Bromoform to iodine ratio (μg/g:ppm) |
|---|---|---|---|---|
| AT Beef Bag 1 | Gametophyte | 2265 | 7961 | 3.5 |
| AT Beef Bag 15 | Gametophyte | 2336 | 7371 | 3.2 |
| AT Beef Bag 21 | Gametophyte | 2201 | 8192 | 3.7 |
| Wild Tetrasporophyte | Tetrasporophyte | * >67.4 | **500-1500 | *<<22.3 |
| AT brominata | Tetrasporophyte | 67.4 | 9600 | 142.4 |

*Because we established that there is a strong inverse correlation between bromoform and iodine content in the types of algal biomass studied here, we assert that the to iodine content of the wild tetrasporophyte assayed here for bromoform is significantly higher than in our AT brominate variant.
**This is the typical range of bromoform that we expect would be found in wild harvested analogous Asparagopsis spp.

Other distinguishing features include the taste and odor of the plant. While naturally occurring, gametophytes tend to be malodorous, our tetrasporophytes have low odor. This is beneficial, since low-odor food tends to be more palatable.

AT tends to grow as epiphytes. The present variety is distinct because it grows as an isolated algae species. This has a number of advantages for algal culture, including the fact that all nutrients go towards the growth of AT rather than competitive species and increased product purity. Nevertheless, AT is a fragile species, highly vulnerable to pests, diseases and competitive algae. The introduction of pests or contaminants may be prevented through a variety of mechanisms such as, but not limited to: purification cycles, maintaining positive air pressure in the flasks, using stoppers on flasks to prevent ingress of materials, wearing lab coats and using shoe dips to prevent pests or contaminants entering the lab. Furthermore, AT has low resistance to shipping or environmental changes. It can be killed or bleached by changes in temperature or light intensity. Given this sensitivity, the plant is grown under controlled environmental conditions. Light is provided by incandescent, halogen, LED, fluorescent, high intensity discharge, metal halide, high pressure sodium or other suitable lights and maintained at 10-100 mE in the seed bank and nursery using 60-80% Blue Pearl shade cloth. Suitably filtered and controlled natural light, if available, properly filtered, and of sufficient duration may also be used as the main, light source, or as a supplement or complement to the artificial light sources named herein, but tightly controlled artificially supplied light is preferable. The photoperiod is maintained at 12 hours per day to prevent spore formation. Within the nursery, flasks are aerated to ensure algae have sufficient supply of $CO_2$ for photosynthesis and $O_2$ for respiration. Aeration also serves to promote movement of biomass. This ensures all algae have access to light, reduces the formation of biofilm, and prevents clumping of algae, which can create an anoxic environment where bacteria or contaminants grow. Nutrients are provided through F/2 medium in approximately the concentrations depicted in Table 2. Temperature is maintained at 65-85° F. (between about 18 and 30° Celsius) throughout the day.

TABLE 2

Concentrations of Nutirents in the F/2 Medium

| Nutrient | Concentration (ml/L) |
|---|---|
| Nitrogen | 6.998 |
| Phosphate | 1.500 |

TABLE 2-continued

Concentrations of Nutirents in the F/2 Medium

| Nutrient | Concentration (ml/L) |
|---|---|
| Vitamin B1 | 0.053 |
| Vitamin B12 | Trace |
| Biotin | Trace |
| Iron* | 0.735 |
| Manganese* | 0.026 |
| Cobalt* | 0.002 |
| Zinc* | 0.003 |
| Copper* | 0.001 |
| Molybdate* | 0.001 |

*Only added for artificial seawater, not deep seawater

Grown under these conditions, the present *Asparagopsis taxiformis* variety is a stable and uniform culture that is distinct from the parent plant. Wild type *Asparagopsis* has unpleasant odor, high iodine content, epiphytic nature, and lack of capacity, especially in male specimens, to synthesize material concentrations of the halogenated compounds. The present variety has higher bromoform content, lower odor, lower iodine, an absence of epiphytes and is static in the tetrasporophyte phase. These anatomically distinguishing features beneficial to cost-effective mass production of a high-quality additive. After this stage, the organisms may be transitioned to outdoor growth.

In one variation the current technology provides for a *Asparagopsis taxiformis* derived biomass with a bromoform to iodine ratio of equal to or greater than about 5:1, 10:1, 15:1, 20:1, 25:1, 50:1, 75:1, 100:1, 150:1, 200:1, 300:1, 400:1, 500:1, 600:1, or 700:1.

In another variation, the current technology provides for a non-filamentous *Asparagopsis taxiformis* derived biomass comprising greater than about 5, about 6, about 7, about 8, about 9, 10, about 11, about 12, about 15, or about 20 mg/g of bromoform w/w of dried material.

In still another variation, the current technology provides for non-filamentous *Asparagopsis taxiformis* tetrasporophyte derived biomass obtained by unattached cultivation in a continuous aeration induced circulatory flow bioreactor.

In one variation, the current technology provides for non-filamentous *Asparagopsis taxiformis* derived biomass continuously grown for 1, 2, 3, 4, 5, 6, 7, 9, or 10 weeks.

The present technology also provides non-filamentous *Asparagopsis taxiformis* algal biomass that is produced through a cultivation cycle comprising a seedbank, nursery, and outdoor phase that spans about 8, 9, 10, 11, 12, 13, 14, 15, 16, 17, 18, 19, 20, 21, 22, 23, or 24 months.

The present technology also provides non-filamentous *Asparagopsis taxiformis* algal biomass that is produced through a cultivation cycle comprising a seedbank, nursery, and outdoor phase that spans more than about 12, 13, 14, 15, 16, 17, 18, 19, 20, 21, 22, 23, or 24 months.

The present technology also provides non-filamentous *Asparagopsis taxiformis* algal biomass that is produced through a cultivation cycle comprising a seedbank, nursery, and outdoor phase that spans more than about 16, 17, 18, 19, 20, 21, 22, 23, or 24 months.

The present technology also provides non-filamentous *Asparagopsis taxiformis* algal biomass that is produced through a cultivation cycle comprising a seedbank, nursery, and outdoor phase that spans more than about 20, 21, 22, 23, or 24 months.

The present technology also provides non-filamentous *Asparagopsis taxiformis* algal biomass that is produced through a continuous cultivation cycle where free-floating tetrasporophytes comprising an acceptable concentration of bromoform may be harvested while leaving the free floating tetrasporophytes that have not achieved acceptable levels of bromoform in the bioreactor for further maturation. The levels of bromoform may include levels from about 3000 to about 20000 µg/g of freeze-dried biomass. In another variation, the levels of bromoform may include levels from about 5000 to about 18000 µg/g of freeze-dried biomass. In another variation, the levels of bromoform may include levels from about 7000 to about 12000 µg/g of freeze-dried biomass. In another variation, the levels of bromoform may include levels from about 9000 to about 11000 µg/mg of freeze-dried biomass. In still another variation, the levels of bromoform may include levels from about 20000 to about 30000 µg/g of freeze-dried biomass.

The present technology also provides non-filamentous *Asparagopsis taxiformis* algal biomass that is produced through a cultivation cycle where the biomass density is less than about 10 g/L in the growth vessels.

In still another variation, the present technology provides for non-filamentous *Asparagopsis taxiformis* algal biomass that is produced through a continuous cultivation cycle at a density of less than about 10 g/l of fresh biomass in a bioreactor for a period of between about 8 months to about 24 months yielding a bromoform content of about between about 9000 µg/g and about 20000 µg/g as measured on the freeze-dried biomass.

In still another variation, the present technology provides for non-filamentous *Asparagopsis taxiformis* algal biomass that is produced through a continuous cultivation cycle at a density of less than about 10 g/l of fresh biomass in a bioreactor for a period of between about 8 months to about 24 months yielding a bromoform content of about between about 2000 µg/g and about 30000 µg/g as measured on the freeze-dried biomass.

Figure 5:
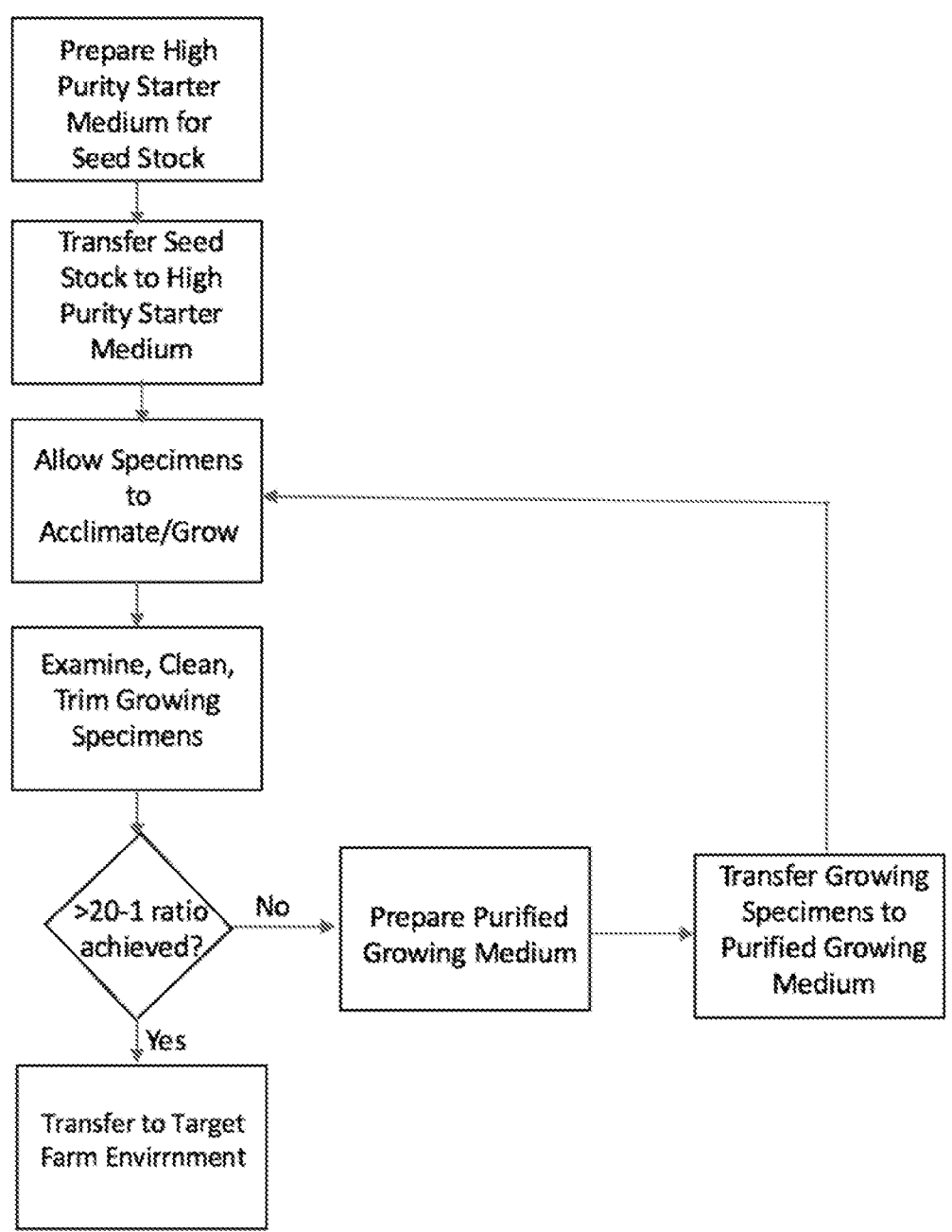
FIG. 5 shows a flow chart of a method for culture enhancement cycles that enable step-wise improvement in the synthesis of halogenated metabolites that forces iodine concentrations lower within target biomass in the tetrasporophyte life stage according to one embodiment of the present technology.

In some embodiments, the present technology relates to a method for cultivating a variety of *Asparagopsis taxiformis* with a higher bromoform concentration, lower odor, lower iodine and higher purity than the parent plants. The features of the variety are suitable for culture in large-scale algaculture and for use as a cattle feed additive. This method comprises 3 phases as shown in FIG. 5:

i) Collection of parent plant;

ii) Manipulation, dissection and growth in a "seed bank" room; and iii) Selection of appropriate material from seed stock.

For the step of collecting the parent plant, wild type *Asparagopsis taxiformis* (AT) is collected from algal turfs or as free-floating algae in the wild. For the step of manipulation, dissection and growth in a "seed bank" room, samples are observed and manipulated under a dissecting microscope to isolate, to the extent possible, clean filaments of AT and separate out contaminants (e.g., epiphytes, other algae, marine animals, contaminated or unhealthy AT). Tiny branches are cut from the mother plant and placed in sterile well plates with seawater, each well containing 360 µL of water. These samples are maintained in a "seed bank" (a room with controlled temperature conditions, contamination protection and carefully-calibrated light with 12-hour photoperiod daily). Cultures are regularly examined. When more than doubled in size, they are stepped-up to larger sterile well plates and then again to sterilized test tubes with 30 ml seawater.

For the step of selecting appropriate material from seed stock, after seven days in test tubes, material that is growing rapidly and, under magnification, appears completely free of epiphytes and fouling organisms is promoted to 250 ml flasks and moved to the nursery. An additional selection step may include selecting for promotion organisms exhibiting larger than usual gland cells. From material that has not achieved those standards, tips representing new growth are cut from the material, which is returned to the smallest sterile well plates with seawater, beginning the process again. The light levels and temperature within the seed bank are controlled to 10-100 µE and 65-85° F. to ensure sustained growth. The growing medium is supplemented with micronutrients in the form of F/2 medium.

As in the seedbank, material in the nursery is grown in an environment that is carefully maintained, including control of light (intensity, spectrum, photoperiod), temperature, micronutrients and aeration. Furthermore, flasks are aerated to ensure algae have sufficient supply of $CO_2$ for photosynthesis and $O_2$ for respiration. Aeration also promotes movement of biomass (beneficial to ensure access to light and prevent formation of biofilm).

Throughout the process, either deep sea water or artificial seawater is used depending on the needs of the plant. Artificial seawater is typically used early in the process when plants are most vulnerable to pests and diseases, and deep seawater later in the process because it contains a rich mix of nutrients that speed plant growth.

In some embodiments, the present technology provides for methods of calculating inclusion rates, methane reduction levels, and methods of intermittent feeding of *Asparagopsis* spp. generally, and more specifically, those disclosed in U.S. provisional patent application 63/117,390 which is incorporated herein in its entirety.

*Asparagopsis* tends to be fed to cows regularly as part of their TMR (total mixed ration). However, recently it was found that the methane-preventing effect of *Asparagopsis* persisted for several days after the cows stopped eating the seaweed. This discovery opens up the possibility of maintaining the same, or similar, impact of *Asparagopsis* supplementation, but with intermittent rather than regular feeding. There are several possible time regimes for this new approach.

Red marine algae contain levels of minerals, energy and macronutrients commensurate with commonly fed grass forage type feedstuffs, such as alfalfa hay and grass hay, except its level of iodine, which is higher than common forages. Seaweeds vary dramatically in iodine concentration, with some having such high levels that they pose a health risk to animals and humans if consumed regularly over long periods of time. Red marine algae appear to be in this regime, with iodine levels as high as 9000 ppm.

Milk iodine levels are directly correlated to iodine intake levels of the cow, with about 2% of consumed iodine being directly passed into the milk. If cows exceed their daily iodine intake levels significantly, their milk will exceed the recommended iodine intake levels for humans. Meat iodine levels from cattle fed a diet including red marine algae at 0.5% of organic matter daily are elevated relative to cattle not fed red marine algae. The concentration of iodine is inversely correlated with the concentration of target components that reduce gas emissions in red marine algae. In one aspect, this target component is bromoform. In another aspect, a target component may be a compound selected from the set of structures illustrated in FIG. 1. The concentration of iodine is generally inversely correlated with the concentration of target components that promote growth performance improvements in red marine algae.

Typically, dairy cows fed algae for methane reduction of about 80% show about 0.9 mg/kg of iodine in their milk when fed algae continuously. Cows not fed algae typically have milk iodine levels of about 0.4 mg/kg. The present investigators found that with an intermittent feeding schedule, a similar level of methane reduction can be achieved while lowering the iodine content of the milk to about 0.8 mg/kg, or less, particularly when the cows are fed the "puffball" morphotype of the *Asparagopsis taxiformis* or *Asparagopsis armata* tetrasporophyte.

In one particular case, it was found that milk from unsupplemented cows contains about 0.3 mg of iodine per kg. On the other hand, milk from cows continuously supplemented with the gametophyte form of *Asparagopsis* spp. to achieve an 80% methane reduction contains about 6.5 mg of iodine per kg. This is an increase of 6.2 mg/kg. With intermittent feeding, feeding every other day, we predict an increase of only 3.1 mg/kg, for a total of about 3.4 mg/kg. Therefore, intermittent feeding methods may also be used alone, or in combination with using algal biomass derived supplements with low iodine content to lower total iodine exposure in supplemented animals.

Red marine algae have complex triphasic life histories with distinct life stages with unique traits and characteristics. Additionally, we have discovered that within some of these life stages, different morphotypes can exist that are particularly effective as feed supplements, especially for promoting efficient growth and methane gas emission reduction in mammals, including ruminants. For red marine seaweeds with a triphasic life history, generations alternate between diploid and haploid stages. The mature haploid, or gametophyte, stage is characterized by a holdfast which resembles a root structure that lodges to a reef or other substrate. In the diploid stage, a tetrasporophyte forms and spreads out around the surrounding turf. Traditional algaculture techniques for red marine algae that will be incorporated into animal feed, human foods and cosmetics mostly rely on the harvest of mixed gender, gametophyte life stage of the plant. Male red marine macroalgal gametophytes contain lower concentrations of the target components that reduce gas emissions in ruminants than do female red marine macroalgae gametophytes. This gametophyte form comprises the holdfast, stipes, and fronds, is a macroscopic form giving rise to the designation "macroalgae". However, in some cases, a particular species of algae may take on microscopic oligocelluar forms which appear to be morphologically and chemotypically very different from the macroalgael form. This morphotype that is particularly useful in the implementation of the current technology is a small red alga comprising branched chains of cells. Unlike the gametophyte form, where cells have differentiated functions (holdfast, stipe, fronds etc.), the cells in the tetrasporophyte are not highly differentiated. Instead, each cluster of four cells is roughly equivalent and these clusters string together into long chains. The color ranges from pale pink to red to dark cherry. Depending on the conditions it is cultivated in, it can take on a "puffball" form, which is distinct from the naturally occurring filamentous form mentioned in the literature. Male red marine macroalgal gametophytes contain lower concentrations of the target components that promote growth performance improvement in ruminants than do female red marine macroalgae gametophytes. Male red marine macroalgal gametophytes contain higher concentrations of nitrogen than do female red marine macroalgae gametophytes. Among all parts of the male and female red marine macroalgal gametophytes, the cystocarps wall of the female have the highest concentration of the target components that reduce gas emissions in ruminants and the lowest concentration of iodine.

Among all parts of the male and female red marine macroalgal gametophytes, the cystocarps wall of the female have the highest concentration of the target components that promote growth performance improvement in ruminants and the lowest concentration of iodine. The carpospores contained within the cystocarps contain virtually no bromoform. The cystocarps of the female gametophytes are club-shaped structures at the tips of the gametophyte fronds. They protrude slightly from the fronds on stems. Effective inclusion of gametophyte-based biomass into animal feeds can be impacted by inadequate concentration of target component to achieve the desired outcomes at cost-effective inclusion rates. The mature gametophyte life stage of red marine macroalgae, both male and female, contains materially higher levels of odor triggering compounds than the tetrasporophyte life stage of the plant. It is thought that these odor triggering compounds comprise iodine or iodide comprising chemical species.

Additionally, the present investigators elucidated how to induce the growth and indefinite maintenance of "puffball" form of the tetrasporophyte that appear to be microscopic oligocellular forms which are very morphologically and chemotypically distinct from the gametophyte macroalgal stage. In particular, the present investigators have discovered that certain of these tetrasporophyte varieties in particular, certain morphotypes, are very well suited for use as feed supplements as a source of halogenated compounds to inhibit methanogenesis, promote growth of animals (e.g., ruminant animals) as well as increase the quality of products derived therefrom.

In view of this, cultivation methods capable of achieving targeted metabolite concentrations are needed to enable effective use of a composition of algae biomass with a ratio of halogenated metabolites μg/g to iodine ppm of greater than about 150:1 at differentially lower levels than 10-30 g/day while minimizing odor and the over-supplementation of iodine.

In some aspects of the present technology, the expected supplementation rates of non-filamentous *Asparagopsis taxiformis* tetrasporophytes, including *Asparagopsis taxiformis* brominata is about 40 g/day, or about 20-60 g/day for dairy cows and less than about 40 g/day for beef cattle. In this case, even though might be supplementation is above 40 g of algae per day in the 20-60 g per day regime, the low iodine content allows for this level of supplementation and results in methane reductions greater than can be achieved by dosing gametophytes or filamentous tetrasporophytes between 10-30 g per day.

In some embodiments, the additional methane reduction is greater than 10%, 20%, 30%, 40%, or 50% over that achieved with the gametophyte or filamentous tetrasporophyte administration at 10-30 g per day while keeping the iodine intake to less than 50 mg/kg of dry matter intake (DMI).

The current technology also includes methods of calculating intermittent dosing schedules that provide for decreased of algal to feed ratios for given methane reduction levels, increased propionate to acetate ratios, and decreased iodine concentrations in milk, meat or fat products derived from the supplemented animals. Inclusion calculation methods capable of achieving targeted component concentrations are needed to enable effective use of red marine algae biomass with a ratio of target components μg/g to iodine ppm of greater than 20:1 so that the biomass can be supplemented at lower levels than 10-30 g/day thus optimizing the concentration of iodine, while enhancing the beneficial effects and minimizing capital and marginal costs.

Algae may contain malodorous components, here called "odor triggering components". These odor triggering components reduce the palatability of the feed that has been supplemented with compositions derived from algal biomass or alga constituents. Therefore, it is desirable to minimize the levels of these components in the final feed either by reducing the concentration of these components in the algal derived composition, or, by enhancing the concentration of the desired bioactive components in relationship to the undesired odor triggering components, thus reducing the amount of the algal derived composition that needs to be added to the animal feed. Described herein are methods and systems of cultivating red marine algae biomass which exhibits the desired characteristics of lower odor, higher halogenated metabolite levels and lower iodine volume than whole plants harvested at the gametophyte stage.

Some embodiments of the present technology include tetrasporophyte life stage algaculture systems. In some implementations of these embodiments, cultivation is achieved in managed systems on land; in others, cultivation is achieved in rack systems on barges, on rafts or in shallow ocean waters. In some embodiments, processes are enabled by an apparatus and in other processes are performed by hand.

In general, embodiments of the methods and systems of the subject disclosure may include establishment of high purity growth media; culture scale selection and isolation of samples for propagation; culture enhancement cycles that enable selection for robustness within target biomass; growth stage control; sustainable harvest; and preservation of halogenated metabolites.

For red marine seaweeds with a triphasic life history, generations alternate between diploid and haploid stages. The mature haploid stage is characterized by a holdfast which resembles a root structure that lodges to a reef or other substrate. In the diploid stage, a tetrasporophyte forms and spreads out around the surrounding turf. As it grows it takes on a form that can be dislodged from the reef, becoming a filamentous free-living organism so different from the gametophyte that it once was considered a different species.

In some embodiments of the present technology, tetrasporophytes are harvested from the ocean or obtained from an in-production biomass generating system. In the ocean, tetrasporophytes grow throughout the water column and may be visible on rocks or on man-made structures including boats and docks. Available samples may be given a cursory inspection for color, purity or texture, as plants that appear healthy and reasonably free of fouling organisms are selected for propagation. Samples may first be placed in bags and bags may be placed on ice during post-collection transport.

Figure 1:
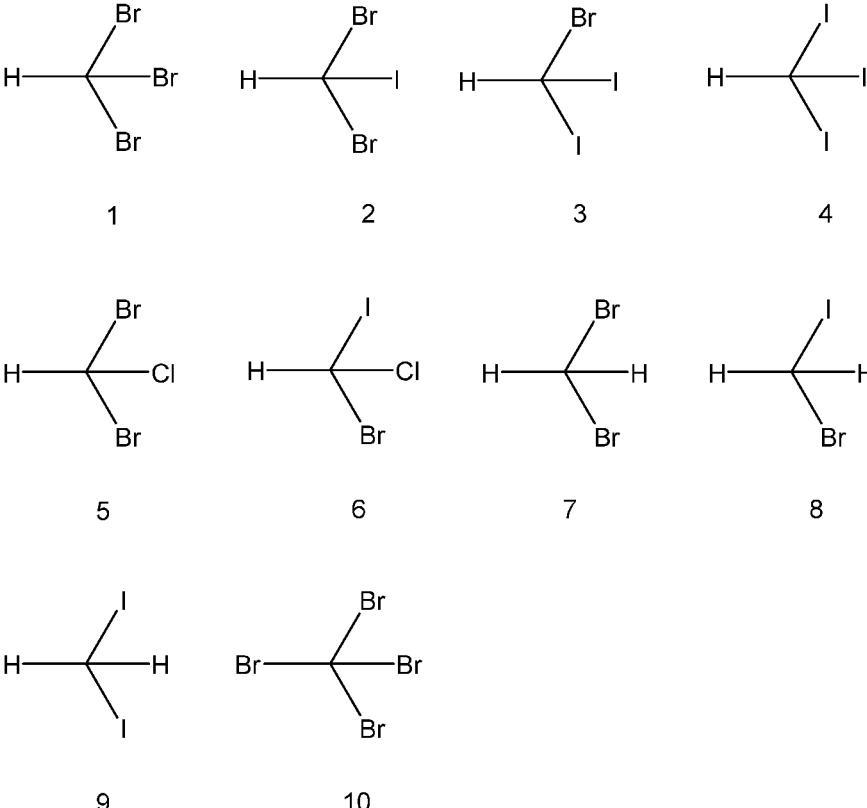
FIG. 1 depicts the target metabolites comprising halogenated metabolites and iodine.

FIG. 5 illustrates a flow chart of a process method for culture enhancement cycles that enable step-wise improvement in the synthesis of halogenated metabolites that forces iodine concentrations lower within target biomass in the tetrasporophyte life stage. The objective of the culture enhancement cycles is to effect stepwise improvement in biomass stock by selecting for robustness within target biomass to promote growth rate and halogenated metabolite accumulation, naturally lowering iodine, while removing non-target species. FIG. 1 illustrates the structures of halogenated metabolites and iodine that may be found in algae. High purity starter medium is prepared for settling the tetrasporophytes into a controlled environment. The water may be nutrient-rich deep ocean water, near-surface seawater, or other saltwater suitable for growing marine species. Collected water is autoclaved, then purified through ultraviolet light. Collected water is further purified through canister filtration. High purity starter medium filtered to 0.2-0.35 microns is brought to an appropriate growth temperature and nutrients are added. Collected tetrasporophytes are removed from bags and added at target densities to small vessels containing the high purity starter medium where they can acclimate to new environmental condition such as light, ambient temperature and biodiversity changes. Purified growing medium is prepared for the cultivation system for the tetrasporophytes. The water may be nutrient-rich deep ocean water, near-surface seawater, or other saltwater suitable for growing marine species. Collected water is autoclaved, then purified through ultraviolet light. Purified growing medium filtered to 0.35-25 microns is brought to an appropriate growth temperature and nutrients are added. After biomass has begun to evidence new growth, laboratory personnel remove specimens singly and examine them under a microscope. Laboratory personnel identify parts of the biomass requiring cleaning, such as the removal of epiphytes or other fouling organisms. Aided by a microscope, tetrasporophytes may be cleaned using tweezers or similar instruments until a level of purity is achieved. Filamentous, or "puffball" forms with robust gland cells may be trimmed and combined in bags or vessels with purified growing medium at a stocking density that promotes growth while inhibiting fouling. The cycle continues, with regular inspections under the microscope, cleaning, and trimming to improve the quality of the algae material and the rate of halogenated metabolite synthesis.

In one embodiment, after sufficient biomass has been produced in smaller and then larger vessels or bags, tetrasporophytes may be transferred to photo bioreactors on land with managed nutrients, lighting, temperature and aeration. As the photobioreactor achieves a stocking density that indicates an appropriate time for harvest, a valve-activated system may be used to release an amount of growing medium from the photobioreactor. Biomass that exits the photobioreactor may be captured in a filter apparatus. Captured biomass is transferred from the filter within minutes to preserve bioactive compounds. Biomass may be blast frozen, then freeze dried under vacuum and temperature control for 30 hours. Biomass may be dried using a vacuum tray dryer. Biomass may be dried in the open sun. Biomass may be dried in a solar conduction dryer. The halogenated metabolites may be extracted from the biomass using oil extraction. The halogenated metabolites may be extracted from the biomass through fractionation.

In one embodiment, biomass that has been combined into a bag or vessel at a stocking density that promotes growth while inhibiting fouling is transferred to racks on rafts or barges or upright in shallow ocean water where nutrients, lighting, and temperature are managed and aeration is enabled by a solar pump. As bags or vessels achieve a stocking density that indicates an appropriate time for harvest, the bags or vessels are removed from racks and the contents are emptied and combined with one another. In one embodiment, the biomass may be blast frozen, then freeze dried under vacuum and temperature control for 30 hours. In one embodiment, the biomass may be dried using a vacuum tray dryer. In one embodiment, the biomass may be dried in the open sun. In one embodiment, the biomass may be dried in a solar conduction dryer. The halogenated metabolites may be extracted from the biomass using oil extraction. In certain embodiments, the oil extract may be used to prepare encapsulated halogenated metabolite containing oil using the methods described herein. The halogenated metabolites may be extracted from the biomass through fractionation.

Inclusion calculation methods capable of achieving targeted metabolite concentrations are needed to enable effective use of a composition of algae biomass with a ratio of non-iodinated halogenated metabolites mg/g to iodine ppm of greater than about 150:1 at differentially lower levels than 10-30 g/day or 20-60 g/day, thus minimizing odor and optimizing palatability.

Animals whose feed is supplemented with the algae biomass, or target components derived therefrom, obtained from these systems and methods provide improvements in the quantity or quality of meat, milk, manure, leather, meal, and fats in addition to reducing harmful methane emissions or example, the milk, meat and manure may have optimal nutritional iodine content and fatty acid composition. Animals fed this feed grow more quickly even on lower quality diets and produce more milk and leather.

In some embodiments, the algae to be feed on an intermittent schedule is a "puffball" or filamentous tetrasporophyte. In one embodiment, the algae is *Asparagopsis armata, Asparagopsis taxiformis, Dictyota* spp (e.g. *Dictyota bartayresii*), *Oedogonium* spp, *Ulva* spp, or *C. patentiramea*. In yet another embodiment, the algae is an *Asparagopsis* species. In yet another embodiment, the algae is *Asparagopsis taxiformis*. In yet another embodiment, the algae is *Asparagopsis armata*.

In one embodiment, the animals supplemented with the compositions of the present technology gain about 1%, 2%, 3%, 4%, 5%, 6%, 7%, 8%, 9%, 10% or 11% more weight than animals fed the same unsupplemented diet. This weight gain difference may be average weight at slaughter or other time in the growth cycle. In one embodiment, the animals supplemented with the compositions of the present technology gain about 12%, 13%, 14%, 15%, 16%, 17%, 18%, 19%, 20% or 21% more weight than animals fed the same unsupplemented diet. This weight gain difference may be average weight at slaughter or other time in the growth cycle.

In one embodiment, the animals supplemented with the compositions of the present technology grow about 1%, 2%, 3%, 4%, 5%, 6%, 7%, 8%, 9%, 10% or 11% faster than animals fed the same unsupplemented diet. This weight gain difference between supplemented and supplemented animals may defined as average daily weight gain. In one embodiment, the animals supplemented with the compositions of the present technology grow about 12%, 13%, 14%, 15%, 16%, 17%, 18%, 19%, 20% or 21% faster than animals fed the same unsupplemented diet. This weight gain difference between supplemented and supplemented animals may defined as average daily weight gain.

In one embodiment, the animals supplemented with the compositions of the present technology provide meat or milk that is about 1%, 2%, 3%, 4%, 5%, 6%, 7%, 8%, 9%, 10% or 11% lower in trans-fat than animals fed the same unsupplemented diet. In one embodiment, the animals supplemented with the compositions of the present technology provide meat or milk about 12%, 13%, 14%, 15%, 16%, 17%, 18%, 19%, 20% or 21% lower in trans-fat than animals fed the same unsupplemented diet.

In another embodiment, the supplemented animals require about 1%, 2%, 3%, 4%, 5%, 6%, 7%, 8%, 9%, 10%, 11%, 12%, 13%, 14%, 15%, 16%, 17%, 18%, 19%, 20% or 21% less feed than normally calculated based on the animal's breed and activity level.

In one embodiment, the animals supplemented with the compositions of the present technology provide meat or milk that is about 10% to 20%, 21% to 30%, 31% to 40%, 41% to 50%, 51% to 60%, 61% to 70%, 71% to 80%, 81% to 90%, 91% to 99% or 100% lower in trans-fat than animals fed the same unsupplemented diet.

In one embodiment, the animals supplemented with the compositions of the present technology have a propionate to acetate ratio in their rumen about 1%, 2%, 3%, 4%, 5%, 6%, 7%, 8%, 9%, 10% or 11% greater than animals fed the same unsupplemented diet. In one embodiment, the animals supplemented with the compositions of the present technology have a propionate to acetate ratio in their rumen about 12%, 13%, 14%, 15%, 16%, 17%, 18%, 19%, 20% or 21% greater than animals fed the same unsupplemented diet. In one embodiment, the animals supplemented with the compositions of the present technology have a propionate to acetate ratio in their rumen about 10% to 20%, 21% to 30%, 31% 40%, 41% to 50%, 51% to 60%, 61% to 70%, 71% to 80%, 81% to 90%, 91% to 99% or 100% greater than animals fed the same unsupplemented diet.

In one embodiment, the animals supplemented with the compositions of the present technology provide about 1%, 2%, 3%, 4%, 5%, 6%, 7%, 8%, 9%, 10% or 11% more milk than animals fed the same unsupplemented diet. In one embodiment, the animals supplemented with the compositions of the present technology provide about 12%, 13%, 14%, 15%, 16%, 17%, 18%, 19%, 20% or 21% more milk than animals fed the same unsupplemented diet.

In one embodiment, the animals supplemented with the compositions of the present technology provide about 22%, 23%, 24%, 25%, 26%, 27%, 28%, 29%, 30% or 31% more milk than animals fed the same unsupplemented diet.

In one embodiment, the ratio of methane-reducing quality-quantity enhancing feed supplements added to animals' normal diet is calculated by the methods, systems, and devices of the present technology. In one embodiment, animals fed the supplemented diet exhale more hydrogen than animals fed the unsupplemented diet.

In one embodiment, the animals supplemented with the compositions of the present technology exhale about 10% to 20%, 21% to 30%, 31% to 40%, 41% to 50%, 51% to 60%, 61% to 70%, 71% to 80%, 81% to 90%, 91% to 99% or 100% more hydrogen than animals fed the same unsupplemented diet. In one embodiment, the animals supplemented with the compositions of the present technology exhale about 1%, 2%, 3%, 4%, 5%, 6%, 7%, 8%, 9%, 10% or 11% more hydrogen than animals fed the same unsupplemented diet. In one embodiment, the animals supplemented with the compositions of the present technology exhale no less than about 1%, 2%, 3%, 4%, 5%, 6%, 7%, 8%, 9%, 10% or 11% of hydrogen than animals fed the same unsupplemented diet. In one embodiment, the animals supplemented with the compositions of the present technology exhale no less than about 10% to 20%, 21% to 30%, 31% to 40%, 41% to 50%, 51% to 60%, 61% to 70%, 71% to 80%, 81% to 90%, 91% to 99% or 100% of hydrogen than animals fed the same unsupplemented diet.

In one embodiment, animals fed the supplemented diet exhale less methane than animals fed the unsupplemented diet.

In one embodiment, the animals supplemented with the compositions of the present technology exhale about 1%, 2%, 3%, 4%, 5%, 6%, 7%, 8%, 9%, 10% or 11% less methane than animals fed the same unsupplemented diet. In one embodiment, the animals supplemented with the compositions of the present technology exhale about 10% to 20%, 21% to 30%, 31% to 40%, 41% to 50%, 51% to 60%, 61% to 70%, 71% to 80%, 81% to 90%, 91% to 99% or 100% less methane than animals fed the same unsupplemented diet. In one embodiment, the animals supplemented with the compositions of the present technology exhale no less than about 1%, 2%, 3%, 4%, 5%, 6%, 7%, 8%, 9%, 10% or 11% of carbon dioxide than animals fed the same unsupplemented diet. In one embodiment, the animals supplemented with the compositions of the present technology exhale no less than about 10% to 20%, 21% to 30%, 31% to 40%, 41% to 50%, 51% to 60%, 61% to 70%, 71% to 80%, 81% to 90%, 91% to 99% or 100% of carbon dioxide than animals fed the same unsupplemented diet.

In one embodiment, the present technology provides for cultivation methods capable of achieving targeted metabolite concentrations needed to enable effective use of a composition of algae biomass with a ratio of the concentration of halogenated metabolites (mg/g) to iodine (ppm) of greater than 150:1, thus allowing the inclusion of the algae biomass in animal feed at lower levels than between about 10 g/day and about 60 g/day therefore minimizing odor and the over-supplementation of iodine while maintaining the beneficial effects of reduced methane generation, faster growth, higher final body mass, fatty acid content quality, manure quality, leather quality, meat quality, and milk quality.

In some embodiments, the inclusion rate may be 10, 15, 20, 25, 30, 35, 40, 45, 50, 55, or 60 g/day on a particular day. In other embodiments, the inclusion rate may be 10, 15, 20, 25, 30, 35, 40, 45, 50, 55, or 60 g/day averaged over 2, 3, 4, 5, 6, or 7-day period. In one embodiment the inclusion rate is about 40 g/day about every 48 h.

In another embodiment, the algal supplement is administered every 1.5 days, every 2 days, every 3 days or every 4.5 days. In still another embodiment, the algal supplement is administered every 7 days. In one embodiment, the inclusion rate is determined by an algorithm in which one input is the amount of neutral detergent fiber (NDF) in the animal's diet. In another embodiment, the amount of neutral detergent fiber in an animal's diet is determined by multiplying the animal's dry matter intake by the percentage of neutral detergent fiber in the dry matter that is fed to the animal.

In still another embodiment, a regression constant is determined. The regression constant relates the amount of bromoform required to achieve a set percentage of methane reduction per amount of neutral detergent fiber present in the animal's diet. Thus, the algorithm comprises the steps of: i) Determining the target methane reduction percentage and subsequently the target absolute reduction (g $CH_4$/kg milk); ii) Determining cow's NDF intake, based on dry matter intake (DMI) and NDF proportion; iii) Determining the normalized bromoform concentration required (equivalent to the desired absolute reduction divided by the regression constant, where the regression constant is the Reduction in methane intensity (g $CH_4$/kg milk) per unit normalized bromoform intake (mg/kg of NDF); iv) Multiplying by the NDF intake to determine the required bromoform concentration (mg) and v) Dividing by the bromoform concentration in that seaweed to determine amount of seaweed required.

The present investigators have found that this algorithm correctly predicts methane reduction whether the algal supplement is fed on a continuous or intermittent schedule as shown in FIG. 12 and FIG. 13.

In one embodiment, the present technology provides for cultivation methods capable of achieving targeted metabolite concentrations are needed to enable effective use of a composition of algae biomass with a ratio of the concentration of non-iodinated halogenated metabolites (mg/g) to iodine (ppm) of greater than 150:1, thus allowing the inclusion of the algae biomass in animal feed at lower levels than between about 10 g/day and about 30 g/day therefore minimizing odor and the over-supplementation of iodine while maintaining the beneficial effects of reduced methane generation, faster growth, higher final body mass, fatty acid content quality, manure quality, leather quality, meat quality, and milk quality.

In one embodiment, the cultivation method of the present technology provides a composition comprising algae biomass with a ratio of the concentration of halogenated metabolites (µg/g) to iodine (ppm) of greater than 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, or 19:1. In one embodiment, the cultivation method of the present technology provides a composition comprising algae biomass with a ratio of the concentration of non-iodinated halogenated metabolites (µg/g) to iodine (ppm) of greater than 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, or 19:1. In one embodiment, the cultivation method of the present technology provides a composition comprising algae biomass with a ratio of the concentration of halogenated metabolites (µg/g) to iodine (ppm) of greater than 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, or 39:1. In one embodiment, the cultivation method of the present technology provides a composition comprising algae biomass with a ratio of the concentration of non-iodinated halogenated metabolites (µg/g) to iodine (ppm) of greater than 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, or 39:1.

In one embodiment, the cultivation method of the present technology provides a composition comprising algae biomass with a ratio of the concentration of bromoform (µg/g) to iodine (ppm) of greater than 20:1. In one embodiment, the cultivation method of the present technology provides a composition comprising algae biomass with a ratio of the concentration of bromoform (µg/g) to iodine (ppm) of greater than 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, or 19:1. In one embodiment, the cultivation method of the present technology provides a composition comprising algae biomass with a ratio of the concentration of bromoform (µg/g) to iodine (ppm) of greater than 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, or 39:1. In one embodiment, the cultivation method of the present technology provides a composition comprising algae biomass with a ratio of the concentration of bromoform (µg/g) to iodine (ppm) of equal to or greater than 700:1, 600:1, 500:1, 400:1, 300:1 200:1, 150:1, 140:1, 130:1, 120:1, 100:1, 75:1, 50:1, 25:1, or 20:1. In a preferred embodiment, the algae biomass obtained by the methods of the present technology has a ratio of concentration of bromoform (µg/g) to iodine (ppm) of greater than 140.

In some embodiments, the present disclosure provides methods of estimating average concentration of target components, the range of component concentrations within the sample, or trending of component concentration levels over time. In some implementations of these embodiments, the methods include measurement or manipulation of the intensity or wavelength distribution spectrum of the light source, measurement or manipulation of the sample turbidity in an image-based target component measurement system, or photobioreactor, or other algae growth vessel. In some implementations of these embodiments, the methods include computer vision-based feature recognition and neural network based optical image analysis.

In some embodiments, the present disclosure provides for methods for triggering alerts or actions based on positive or negative developments of the measurement of target components within the microalgae or algae sample. In some implementations of these embodiments, the methods include triggering a cultivation harvesting cycle, adjustment of environmental conditions, or request for personnel intervention.

As used herein, the expression "target component" includes halogenated metabolites, iodine, bromoform or other components of pre-harvest, post-harvest, or post processed algae biomass that are determined to affect the function of the derived composition as an animal feed supplement.

When a ratio of halogenated metabolites to iodine is referred to, the halogenated metabolites include iodine containing compounds, but not elemental iodine. When a ratio of non-iodinated halogenated metabolites to iodine is referred to, the non-iodinated halogenated metabolites exclude iodine containing compounds and elemental iodine. When a ratio of non-iodinated halogenated metabolites to iodine is referred to, the iodine content comprises any target component that contains iodine, including elemental iodine, organic iodine and inorganic iodine.

In one embodiment, the expression "inorganic iodine" means iodide anions, salts, hypoiodites and the like. In one embodiment, the expression "organic iodine" refers to any compound comprising at least one iodine atom bound to at least one carbon atom.

The target components may be metabolite components contained within algae, microalgae, or algae. Target component includes, but is not be limited to: primary metabolites, secondary metabolites, substances absorbed or concentrated from the environment, substances present due to the actions of parasites or symbiotes, substances formed due to environmental factors, substances formed through the actions of electromagnetic radiation; acoustic energy; fermentation by bacteria, yeasts or other organisms; oxidation, dehydration, elimination, hydration, decarboxylation, isomerization, racemization, chelation, inclusion, fragmentation; or substances that are substrates for the actions of electromagnetic radiation; acoustic energy; fermentation by bacteria, yeasts or other organisms; oxidation, dehydration, elimination, hydration, decarboxylation, isomerization, racemization, chelation, inclusion, fragmentation. In one embodiment, a target component is bromoform. In one embodiment, a target component is a halogenated metabolite. In one embodiment, a target component is a non-iodinated metabolite. In another embodiment, a target component is elemental iodine ($I_2$). In another embodiment, a target component is organic iodine. In another embodiment, a target component is inorganic iodine. In another embodiment, a target component is a substance that liberates elemental iodine post-harvest of the algae biomass. A representative set of target components is shown in FIG. 1. Without wishing to be bound by theory, it is thought that bromoform (compound 1) is a major contributor to the methane reduction and animal product improvement results of seaweed supplementation.

The terms "level" and "levels" may mean an absolute level, an amount over time, or a concentration, depending on context. For example, when referring to "levels of consumption", the term "levels" should be construed as an amount eaten by an animal over a set period of time, such as a day, a week, month, etc., when referring to a level of a component in algal biomass, the term "level" means the concentration of that component in a particular weight or volume of biomass. In the last case, the level may be determined on living biomass in a photoreactor, wet harvested biomass, dried biomass, or biomass at each stage of processing from start to the final commercial product.

In some embodiments, the inclusion calculations can take into account the addition of other, non-algae derived components that provide additive or synergistic beneficial effects when combined with the compositions described herein. In some embodiments, the non-algae derived components are selected from the group consisting of; 3-nitrooxypropanol, Mootral (a product of Mootral, a Swiss Agritech company), garlic extract, Yucca extract, Yucca powder, saponin, furostanol aglycone, spirostanol aglycone, chloroform, sarsapogenin, markogenin, smilagenin, samogenin, gitogenin, neogitogenin, monodesmosidic saponins, YS-I, YS-II, YS-III, YS-IV, YS-V, YS-VI, YS-VII, YS-VIII, YS-IX, YS-X, YS-XI, YS-XII, YS-XIII, bidesmoside saponin components, monodesmoside saponin components, quillaya saponins, proanthocyanidins, condensed tannins, hydrolysable tannins, Gynosaponins powder, Tea saponin, *Sesbania sesban* leaves extract, *Acacia mearnsii* extract, *Acasia saligna* leaves, *Leucaena leucocephala* extracts, *Lespedeza striata* forage, Combination of essential oil (809 g/kg eugenol in thyme oil; 837 g/kg carvacrol in oregano oil; 855 g/kg cinnamaldehyde in cinnamon oil; 801 g/kg limonene in lemon oil) plus monosodium fumarate, Combination of essential oil (eugenol, carvacrol, citral, cinnamaldehyde; purity 0.99%) plus monosodium fumarate, Agolin Ruminant (Agolin S. A. Of Biere, Switzerland) and *Mentha microphylla* (piperitone oxide and cis-piperitone oxide—46.7% and 28%).

In some embodiments, the compositions of the present technology may be used in combination with other methane-reducing, quality and quantity enhancing components as disclosed in A. Cieslak, M. Szumacher-Strabel, A. Stochmal and W. Oleszek, Animal (2013), 7: s2, pp 253-265 & The Animal Consortium 2013, doi: 10.1017/S1751731113000852, which is incorporated herein in its entirety.

Red algae, in contrast to green and brown algae, produce a broad set of halogenated metabolites including peptides, polyketides, indoles, terpenes, phenols and volatile halogenated hydrocarbons. One of the prominent halogenated metabolites of *Asparagopsis taxiformis* is the halogenated hydrocarbon Bromoform, $CHBr_3$. The concentrations of Bromoform and other halogenated compounds present in

*Asparagopsis taxiformis* and other red algae have been shown to vary widely based on the growth environment, seasonality, species, strain, lifestage, cultivation method, and other known and unknown factors.

In vitro and in vivo testing has identified a strong positive correlation between the level of methane reduction in ruminants and the ratio of the bromoform component delivered from a red algae feed supplement relative to specific types of the animal's diet such as pasture derived fee and finishing diets. However, it has not until our work, that the specific component determinants of these interactions have been identified.

In vivo testing has identified a strong positive correlation between the level of methane reduction in ruminants and the ratio of the bromoform component delivered from a red algae feed supplement, relative to specific components of the animal's diet. In vivo testing has identified a predictive relationship among the concentration of bromoform in algae, neutral detergent fiber (NDF) in livestock diets, and the percentage of enteric methane reduced.

In vivo testing has identified a predictive relationship among the concentration of bromoform in algae, neutral detergent fiber (NDF) in livestock diets, and the percentage of enteric methane reduced.

The predictive relationship among the concentration of bromoform in algae, neutral detergent fiber (NDF) in livestock diets, and the percentage of enteric methane reduced is consistent within livestock that share common characteristics related to species, breed, gender, age, and stage of reproductive cycle.

It is known that bromoform is safely and usefully degraded in anaerobic environments like livestock rumens where the enzyme methyl-coenzyme M reductase is present. As evidenced by in vitro and in vivo testing, the degradation of the bromoform component delivered from red algae beneficially increases the propionate:acetate ratios in livestock rumens, which enables conservation of feed energy.

It has been further evidenced from the testing of meat from beef steers fed a red algae containing bromoform that the increase in propionate:acetate ratios in livestock rumens results in lower trans fat metabolized in meat.

Measurement and informed management of metabolite component concentrations in red algae during cultivation and in livestock feed and supplement formulation are critical to achieving safe, impactful, and cost-effective use of red algae as a feed supplement for mitigating methane emissions or delivering other targeted benefits.

The ability to accurately calculate and account for reductions in greenhouse gas emissions that result from livestock which consume red macroalgae is therefore critical to those persons, governmental bodies, non-governmental bodies, and private corporations that value such reductions in greenhouse gas emissions.

Described herein is a system and method that calculates and accounts for the enteric methane emissions that result from livestock which consume red macroalgae.

The components of this system and method include a knowledge base of the interrelationships among variables related to red macroalgae, inclusion rates of red macroalgae, and livestock diets, as well as the combinatorial impact of these variables on livestock enteric methane emissions; an algorithm that calculates enteric methane emissions based on the interrelationships among variables related to red macroalgae, inclusion rates of red macroalgae, and livestock diets; and a system that accounts for enteric methane emissions reductions that result from livestock which consume red macroalgae.

In one embodiment, the system calculates the enteric methane reductions that result from a certain inclusion rate of red macroalgae in livestock feed and supplements.

In one embodiment, the system documents, accounts, tracks and verifies enteric methane emissions from livestock which consume red macroalgae. Further embodiments include integration with digital or analogue processes that document, account, track and verify methane emissions reductions from livestock which consume red macroalgae. In some embodiments, processes that document, account, track, and verify enteric methane emissions reductions from livestock which consume red macroalgae operate dependently on other, existing systems. In other embodiments they operate independently of other, existing systems.

In one embodiment, the system is accessed by a graphical user interface. In another embodiment, the system is accessed by an application programming interface. Further embodiments enable and allow users to enter and manipulate input data and objective functions, and to observe the results of an algorithmic calculation based on those inputs.

Shown in FIG. 10 is an embodiment of a system (1) of the present technology that calculates and accounts for the enteric methane emissions reductions that result from livestock which consume red macroalgae. The system includes a knowledge base and algorithm (11) that calculates the enteric methane reductions that result from a certain inclusion rate of red macroalgae in livestock feed and supplements. This knowledge base and algorithm (11) is programmed into computer software (12) which resides and is accessed on a mainframe computer server (13). In one embodiment, a database (16) which resides on the mainframe computer (13) documents, accounts, tracks, and verifies enteric methane emissions from livestock which consume red macroalgae. In this embodiment, system users may input data (14) into the database (16) through a unique graphical interface (15) or through an existing software program (18) that is capable of electronic data interchange (17). In one embodiment, users of the system receive a unique identification number associated with their data. In a further embodiment, this unique identification number is used for verifying and tracking livestock enteric methane emissions reductions.

Currently, there also does not exist a system and method that precisely calculates the inclusion rate of red algae in livestock feed and supplements to achieve specific desired biological impacts and outcomes. The ability to precisely formulate the inclusion rate of red algae in livestock feed and supplements is therefore critical to those persons responsible for animal health and the economic viability of livestock feeding operations.

Described herein is a system and method that calculates precise inclusion rates of red algae in livestock feed and supplements. This system and method accounts for variables related to red algae and livestock diets in ways that deliver specific intended biological impacts and outcomes to livestock and their byproducts.

The system also comprises supplementation schedules which may be intermittent or continuous.

In one embodiment, intermittent feeding, is where the variation in feeding is done on a daily or weekly timescale. For example, one might imagine feeding *Asparagopsis* in the morning TMR but not the evening, or on weekdays but not weekends. This could yield a number of the benefits above, for example reducing labor. Note that, though the actual feeding of the *Asparagopsis taxiformis* (AT) is done on sub-week timescales, this will likely be part of a feeding regimen lasting a couple weeks or more.

In another embodiment, intermittent feeding, is where the variation in feeding is done on a period of longer than a week. For example, one might imagine feeding *Asparagopsis* during lactation but not during pregnancy for dairy cows or removing beef steers from the feed additive two weeks before harvest.

In still another embodiment, feeding ruminants a higher dose of *Asparagopsis* at the beginning of the dosing period, tapering to a lower dose towards the end of the dosing period. This could be useful, for example, to "kickstart" the benefits of AT.

In another embodiment, feeding ruminants a lower dose of *Asparagopsis* at the beginning of the dosing period, increasing to a higher dose at the end of the dosing period. This could be useful, for example, to maintain or elongate the benefits of AT.

In still another embodiment, the current technology is used to alter the dose of AT based on the concentration of the active ingredient (bromoform) within the seaweed.

In one embodiment, the current technology provides for a more efficacious use of AT as calculated by the methane reduction per gram of AT composition fed per animal.

In one embodiment, the increase of efficacy of the amount of methane emissions reduced per gram of the AT composition is at least about 5%, 10%, 20%, 30%, 40%, 50%, 75%, 100%, 150%, 200% or greater than 200%.

In still another embodiment, the method of feeding ruminant animals a time-varying dose of AT composition.

In one embodiment, a time varying dose of AT composition is a supplementation schedule describing the regularly occurring intervals and amounts of feeding the AT composition.

In another embodiment, the AT composition is administered once every 48 h.

In still another embodiment, the AT composition is administered every 72 h.

In another embodiment, a time varying dose of AT composition is a supplementation schedule describing the supplementation time window and dose of the AT composition based on discrete events such as reproductive status or time to market, or other such events that would limit the amount of iodine or halogenated organic materials allowable in the animal product or animal.

In another embodiment, the time varying dose supplementation schedule time window is adjusted to comport with animal feed regulations or consumer perception.

In still another embodiment, the current technology allows for the more flexible crew scheduling since fewer crew members would be required to be familiar with the AT composition administration.

In one embodiment, the current technology provides for healthier animals and their offspring as compared to unsupplemented or continuously supplemented animals.

In still another embodiment, the current technology provides for higher quality animal products compared to unsupplemented or continuously supplemented animals.

In another aspect, the feed supplement compositions of the present technology do not comprise sweeteners, such as, but not limited to, molasses, high fructose corn syrup, sucrose, fructose, xylitol, sorbitol, or other sugars or alcohol sugar appetants.

In another aspect, the feed supplement compositions of the present technology may comprise sweeteners, such as, but not limited to, molasses, high fructose corn syrup, sucrose, fructose, xylitol, sorbitol, or other sugars or alcohol sugar appetants.

In yet another aspect, the feed supplement compositions of the present technology may be used to supplement feedlot animals on finishing diets at a daily supplementation rate of less than 200 g/day, less than about 150 g/day, less than about 100 g/day, or about or less than about 50 g/day of the algal biomass described here for animals on finishing diets.

The components of this system and method include a knowledge base of the interrelationships among variables related to red algae, variables related to inclusion rates of red algae, variables related to livestock diets, as well as the combinatorial impact of these variables on specific biological outcomes to livestock and their byproducts; an algorithm that calculates and predicts specific biological impact and outcomes to livestock and their byproducts based on the interrelationships among variables related to red algae, inclusion rates of red algae, and livestock diets; and guidance for persons skilled in the art of formulating livestock feed and supplements that achieves specific and intended biological impact and outcomes to livestock and their byproducts.

In one embodiment, the system calculates and predicts the enteric methane reductions that result from a certain inclusion rate of red algae in livestock feed and supplements.

In one embodiment, the system calculates and predicts specific improvements in livestock feed conversion efficiency ratios, or improvements in livestock productivity gains and outputs that result from a certain inclusion rate of red algae in livestock feed and supplements.

In one embodiment, the system calculates and predicts propionate:to acetate ratios in livestock rumens that result from a certain inclusion rate of red algae in livestock feed and supplements.

In one embodiment, the system calculates and predicts valuable attributes in the byproducts of livestock that result from a certain inclusion rate of red algae in livestock feed and supplements.

In a further embodiment, the system calculates and predicts valuable attributes in the meat and milk produced by livestock which have consumed a certain inclusion rate of red algae in their feed and supplements.

In one embodiment, the system calculates and predicts economically optimal inclusion rates of red algae in livestock feed and supplements.

In one embodiment, the system calculates and formulates livestock feed and supplement rations in which red algae is added. Further embodiments include integration with digital or analogue processes that calculate and formulate livestock feed and supplement rations. In some embodiments, calculations and formulations operate dependently on other existing systems. In other embodiments they operate independently of other, existing systems.

In one embodiment, the system is accessed by a graphical user interface. In another embodiment, the system is accessed by an application programming interface. Further embodiments enable and allow users skilled in the art of formulating livestock feed and supplements to enter and manipulate input data and objective functions, and to observe the results of an algorithmic calculation based on those inputs.

In one embodiment, the system is used by commercial feed mills.

In another embodiment, the system is used in on-farm feeding operations.

Shown in FIG. 11 is an embodiment of a system (1) that calculates precise inclusion rates of red algae in livestock feed and supplements. The system includes a knowledge base and algorithm (11) that calculates and predicts specific biological impact and outcomes to livestock and/or their byproducts based on the interrelationships among variables related to red algae, inclusion rates of red algae, and livestock diets. This knowledge base and algorithm (11) is programmed into computer software (12) which resides and is accessed on a mainframe computer server (13). In one embodiment, the knowledge base and algorithm provides instructions (14) to persons skilled in the art of formulating livestock feed and supplements for incorporating red algae into livestock feed and supplements. In this embodiment, instructions are based on common characteristics related to species, breed, gender, age, and stage of reproductive cycle, as well as predetermined objective functions related to specific intended biological impact and outcomes to livestock which possess these common characteristics and/or the byproducts produced by livestock which possess these common characteristics. In another embodiment, a unique graphical user interface (15) allows users skilled in the art of formulating livestock feed to enter and manipulate input data and objective functions, and to observe the results (16) rendered by the knowledge based and algorithm (11). In another embodiment, the knowledge base and algorithm are accessed by an application programming interface (17) and the observed results are rendered and observed within an existing software program (18).

Shown in FIG. 1, are exemplary structures of the halogenated metabolites and other halogen containing compounds that are a subset of the target compounds whose levels are an input into the methods of the present technology that calculate their levels of inclusion in the feed supplements and supplemented feeds of the present technology.

The current technology also includes novel varieties of AT that are particularly suitable for intermittent feeding.

Animals may be sensitive to changes in routine, especially sudden changes to their diet. While continuous supplementation with additives having distinctive odors may be initiated with a gradual increase in addition rate, the type of intermittent feeding schedules contemplated herein may cause animals to reject feed supplemented with odiferous additives. Here, the compositions of the current technology avoid these issues by containing low concentrations of malodorous components, thus allowing for flexible schedules of intermittent feeding.

In certain embodiments, the compositions of the current technology comprise non-gametophyte derived algal biomass exhibiting a bromoform content of more than 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, or 0.1 w/w % dry weight.

In certain embodiments, the compositions of the current technology comprise non-gametophyte derived algal biomass exhibiting a bromoform content of more than 1.8 w/w % dry weight.

In certain embodiments, the compositions of the current technology comprise non-gametophyte derived algal biomass exhibiting an iodine content of less than 0.1, 0.09, 0.08, 0.07, 0.06, 0.05, 0.04, 0.03, 0.02 or 0.01 w/w % dry weight.

In certain embodiments, the compositions of the current technology comprise non-gametophyte derived algal biomass exhibiting an iodine content of less than 0.145 w/w % dry weight.

In certain embodiments, the compositions of the current technology comprise algal biomass exhibiting an iodine to bromoform ratio of less than 0.1, 0.09, 0.08, 0.07, 0.06, 0.05, 0.04, 0.03, 0.02, 0.012 or 0.01.

More preferably, the compositions of the current technology comprise algal biomass exhibiting an iodine to bromoform ratio of less than 0.04, 0.03, 0.02, 0.012 or 0.01.

Even more preferably, the compositions of the current technology comprise algal biomass exhibiting an iodine to bromoform ratio of less than 0.012.

In some embodiments, the iodine content of the algal biomass may comprise elemental iodine, organic iodine compounds, inorganic iodine compounds, iodide, iodate or periodate, or a combination thereof.

In some embodiments, the iodine content of the algal biomass may liberate elemental iodine upon harvesting, processing, or storage.

In certain embodiments, the current technology provides for a method of reducing methane reductions from ruminants by at least 80% by supplementing the food rations of such ruminants with non-gametophyte derived algal biomass exhibiting a bromoform content of more than 2.5, 2.4, 2.3, 2.2, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, or 0.1 w/w % dry weight.

In certain embodiments, the current technology provides for a method of reducing methane reductions from ruminants by at least 80% by supplementing the food rations of such ruminants with non-gametophyte derived algal biomass exhibiting an iodine content of less than 0.1, 0.09, 0.08, 0.07, 0.06, 0.05, 0.04, 0.03, 0.02 or 0.01 w/w %.

In certain embodiments, the current technology provides for a method of reducing methane reductions from ruminants by at least 80% by supplementing the food rations of such ruminants with algal biomass exhibiting an iodine to bromoform ratio of less than 0.1, 0.09, 0.08, 0.07, 0.06, 0.05, 0.04, 0.03, 0.02, 0.012 or 0.01.

More preferably, the current technology provides for a method of reducing methane reductions from ruminants by at least 80% by supplementing the food rations of such ruminants with algal biomass exhibiting an iodine to bromoform ratio of less than 0.04, 0.03, 0.02, 0.012 or 0.01.

Even more preferably, the current technology provides for a method of reducing methane production from ruminants by at least 80% by supplementing the food rations of such ruminants with algal biomass such that the ruminant consumes less than 50 mg of iodine per 1 kg of dry matter intake.

Even more preferably, the current technology provides for a method of reducing methane production from ruminants by at least 80% by supplementing the food rations of such ruminants with algal biomass such that the ruminant consumes less than 40 mg of iodine per 1 kg of dry matter intake.

Even more preferably, the current technology provides for a method of reducing methane production from ruminants by at least 80% by supplementing the food rations of such ruminants with algal biomass such that the ruminant consumes less than 30 mg of iodine per 1 kg of dry matter intake.

Even more preferably, the current technology provides for a method of reducing methane production from ruminants by at least 80% by supplementing the food rations of such ruminants with algal biomass such that the ruminant consumes less than 20 mg of iodine per 1 kg of dry matter intake.

Even more preferably, the current technology provides for a method of reducing methane production from ruminants by at least 80% by supplementing the food rations of such ruminants with algal biomass such that the ruminant consumes less than 10 mg of iodine per 1 kg of dry matter intake.

Even more preferably, the current technology provides for a method of reducing methane production from ruminants by at least 80% by supplementing the food rations of such ruminants with algal biomass such that the ruminant consumes less than 5 mg of iodine per 1 kg of dry matter intake.

Even more preferably, the current technology provides for a method of reducing methane production from ruminants by at least 80% by supplementing the food rations of such ruminants with algal biomass such that the ruminant consumes less than 4 mg of iodine per 1 kg of dry matter intake.

Even more preferably, the current technology provides for a method of reducing methane reductions from ruminants by at least 80% by supplementing the food rations of such ruminants with algal biomass such that the ruminant consumes less than 3 mg of iodine per 1 kg of dry matter intake.

Even more preferably, the current technology provides for a method of reducing methane production from ruminants by at least 80% by supplementing the food rations of such ruminants with algal biomass such that the ruminant consumes less than 2 mg of iodine per 1 kg of dry matter intake.

Even more preferably, the current technology provides for a method of reducing methane production from ruminants by at least 80% by supplementing the food rations of such ruminants with algal biomass such that the ruminant consumes less than 1 mg of iodine per 1 kg of dry matter intake.

In certain embodiments, the current technology provides for a method of reducing methane production from ruminants by at least 70% by supplementing the food rations of such ruminants with non-gametophyte derived algal biomass exhibiting a bromoform content of more than 2.5, 2.4, 2.3, 2.2, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, or 0.1 w/w % dry weight.

In certain embodiments, the current technology provides for a method of reducing methane production from ruminants by at least 70% by supplementing the food rations of such ruminants with non-gametophyte derived algal biomass exhibiting an iodine content of less than 0.1, 0.09, 0.08, 0.07, 0.06, 0.05, 0.04, 0.03, 0.02 or 0.01 w/w %.

In certain embodiments, the current technology provides for a method of reducing methane production from ruminants by at least 70% by supplementing the food rations of such ruminants with algal biomass exhibiting an iodine to bromoform ratio of less than 0.1, 0.09, 0.08, 0.07, 0.06, 0.05, 0.04, 0.03, 0.02, 0.012 or 0.01.

More preferably, the current technology provides for a method of reducing methane production from ruminants by at least 70% by supplementing the food rations of such ruminants with algal biomass exhibiting an iodine to bromoform ratio of less than 0.04, 0.03, 0.02, 0.012 or 0.01.

Even more preferably, the current technology provides for a method of reducing methane production from ruminants by at least 70% by supplementing the food rations of such ruminants with algal biomass such that the ruminant consumes less than 50 mg of iodine per 1 kg of dry matter intake.

Even more preferably, the current technology provides for a method of reducing methane production from ruminants by at least 70% by supplementing the food rations of such ruminants with algal biomass such that the ruminant consumes less than 40 mg of iodine per 1 kg of dry matter intake.

Even more preferably, the current technology provides for a method of reducing methane production from ruminants by at least 70% by supplementing the food rations of such ruminants with algal biomass such that the ruminant consumes less than 30 mg of iodine per 1 kg of dry matter intake.

Even more preferably, the current technology provides for a method of reducing methane production from ruminants by at least 70% by supplementing the food rations of such ruminants with algal biomass such that the ruminant consumes less than 20 mg of iodine per 1 kg of dry matter intake.

Even more preferably, the current technology provides for a method of reducing methane production from ruminants by at least 70% by supplementing the food rations of such ruminants with algal biomass such that the ruminant consumes less than 10 mg of iodine per 1 kg of dry matter intake.

Even more preferably, the current technology provides for a method of reducing methane production from ruminants by at least 70% by supplementing the food rations of such ruminants with algal biomass such that the ruminant consumes less than 5 mg of iodine per 1 kg of dry matter intake.

Even more preferably, the current technology provides for a method of reducing methane production from ruminants by at least 70% by supplementing the food rations of such ruminants with algal biomass such that the ruminant consumes less than 4 mg of iodine per 1 kg of dry matter intake.

Even more preferably, the current technology provides for a method of reducing methane production from ruminants by at least 70% by supplementing the food rations of such ruminants with algal biomass such that the ruminant consumes less than 3 mg of iodine per 1 kg of dry matter intake.

Even more preferably, the current technology provides for a method of reducing methane production from ruminants by at least 70% by supplementing the food rations of such ruminants with algal biomass such that the ruminant consumes less than 2 mg of iodine per 1 kg of dry matter intake.

Even more preferably, the current technology provides for a method of reducing methane production from ruminants by at least 70% by supplementing the food rations of such ruminants with algal biomass such that the ruminant consumes less than 1 mg of iodine per 1 kg of dry matter intake.

In certain embodiments, the current technology provides for a method of reducing methane production from ruminants by at least 85% by supplementing the food rations of such ruminants with non-gametophyte derived algal biomass exhibiting a bromoform content of more than 2.5, 2.4, 2.3, 2.2, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, or 0.1 w/w % dry weight.

In certain embodiments, the current technology provides for a method of reducing methane production from ruminants by at least 85% by supplementing the food rations of such ruminants with non-gametophyte derived algal biomass exhibiting an iodine content of less than 0.1, 0.09, 0.08, 0.07, 0.06, 0.05, 0.04, 0.03, 0.02 or 0.01 w/w %.

In certain embodiments, the current technology provides for a method of reducing methane production from ruminants by at least 85% by supplementing the food rations of such ruminants with algal biomass exhibiting an iodine to bromoform ratio of less than 0.1, 0.09, 0.08, 0.07, 0.06, 0.05, 0.04, 0.03, 0.02, 0.012 or 0.01.

More preferably, the current technology provides for a method of reducing methane production from ruminants by at least 85% by supplementing the food rations of such ruminants with algal biomass exhibiting an iodine to bromoform ratio of less than 0.04, 0.03, 0.02, 0.012 or 0.01.

Even more preferably, the current technology provides for a method of reducing methane production from ruminants by at least 85% by supplementing the food rations of such ruminants with algal biomass such that the ruminant consumes less than 50 mg of iodine per 1 kg of dry matter intake.

Even more preferably, the current technology provides for a method of reducing methane production from ruminants by at least 85% by supplementing the food rations of such ruminants with algal biomass such that the ruminant consumes less than 40 mg of iodine per 1 kg of dry matter intake.

Even more preferably, the current technology provides for a method of reducing methane production from ruminants by at least 85% by supplementing the food rations of such ruminants with algal biomass such that the ruminant consumes less than 30 mg of iodine per 1 kg of dry matter intake.

Even more preferably, the current technology provides for a method of reducing methane production from ruminants by at least 85% by supplementing the food rations of such ruminants with algal biomass such that the ruminant consumes less than 20 mg of iodine per 1 kg of dry matter intake.

Even more preferably, the current technology provides for a method of reducing methane production from ruminants by at least 85% by supplementing the food rations of such ruminants with algal biomass such that the ruminant consumes less than 10 mg of iodine per 1 kg of dry matter intake.

Even more preferably, the current technology provides for a method of reducing methane production from ruminants by at least 85% by supplementing the food rations of such ruminants with algal biomass such that the ruminant consumes less than 5 mg of iodine per 1 kg of dry matter intake.

Even more preferably, the current technology provides for a method of reducing methane production from ruminants by at least 85% by supplementing the food rations of such ruminants with algal biomass such that the ruminant consumes less than 4 mg of iodine per 1 kg of dry matter intake.

Even more preferably, the current technology provides for a method of reducing methane production from ruminants by at least 85% by supplementing the food rations of such ruminants with algal biomass such that the ruminant consumes less than 3 mg of iodine per 1 kg of dry matter intake.

Even more preferably, the current technology provides for a method of reducing methane production from ruminants by at least 85% by supplementing the food rations of such ruminants with algal biomass such that the ruminant consumes less than 2 mg of iodine per 1 kg of dry matter intake.

Even more preferably, the current technology provides for a method of reducing methane production from ruminants by at least 85% by supplementing the food rations of such ruminants with algal biomass such that the ruminant consumes less than 1 mg of iodine per 1 kg of dry matter intake.

In a preferred embodiment, the present technology provides for an algal feed supplement for beef cattle, dairy cattle and other ruminants comprising a maximum of 3000 ppm of iodine by dry weight.

In a preferred embodiment, the present technology provides for an algal feed supplement for beef cattle, dairy cattle and other ruminants comprising a maximum of 2000 ppm of iodine by dry weight.

In a preferred embodiment, the present technology provides for an algal feed supplement for beef cattle, dairy cattle and other ruminants comprising a maximum of 1000 ppm of iodine by dry weight.

In a preferred embodiment, the present technology provides for an algal feed supplement for beef cattle, dairy cattle and other ruminants comprising a maximum of 500 ppm of iodine by dry weight.

In another preferred embodiment, the present technology provides for an algal feed supplement for beef cattle, dairy cattle and other ruminants comprising a minimum of 2.5% of bromoform by dry weight.

In another preferred embodiment, the present technology provides for an algal feed supplement for beef cattle, dairy cattle and other ruminants comprising a minimum of 3.5% of bromoform by dry weight.

In another preferred embodiment, the present technology provides for an algal feed supplement for beef cattle, dairy cattle and other ruminants comprising a minimum of 16% of protein by dry weight.

In another preferred embodiment, the present technology provides for an algal feed supplement for beef cattle, dairy cattle and other ruminants comprising a minimum of 20% of aNDF by dry weight.

In still another preferred embodiment, the present technology provides for an algal feed supplement for beef cattle, dairy cattle and other ruminants comprising a minimum of 20% of aNDF by dry weight, a minimum of 16% protein by dry weight, a maximum of 3000 ppm iodine by dry weight, and a minimum of 2.5% bromoform by dry weight.

In still another preferred embodiment, the present technology provides for a method of reducing methane belching by ruminants comprising supplementing the feed of such ruminants with an algal feed supplement comprising a minimum of 20% of aNDF by dry weight, a minimum of 16% protein by dry weight, a maximum of 3000 ppm iodine by dry weight, and a minimum of 2.5% bromoform by dry weight.

In still another preferred embodiment, the present technology provides for a method of reducing methane belching by ruminants by at least 50% comprising supplementing the feed of such ruminants with an algal feed supplement comprising a minimum of 20% of aNDF by dry weight, a minimum of 16% protein by dry weight, a maximum of 3000 ppm iodine by dry weight, and a minimum of 2.5% bromoform by dry weight.

In still another preferred embodiment, the present technology provides for a method of reducing methane belching by ruminants by at least 80% comprising supplementing the feed of such ruminants with an algal feed supplement comprising a minimum of 20% of aNDF by dry weight, a minimum of 16% protein by dry weight, a maximum of 3000 ppm iodine by dry weight, and a minimum of 2.5% bromoform by dry weight at an average rate of 40 g. per day.

In another embodiment, the present technology provides for a kit comprising an algal feed supplement comprising a minimum of 20% of aNDF by dry weight, a minimum of 16% protein by dry weight, a maximum of 3000 ppm iodine by dry weight, and a minimum of 2.5% bromoform by dry weight accompanied by instructions for substituting the algal feed supplement for total mixed ration (TMR) up to about 0.5% as fed.

In another embodiment, the present technology provides for a kit comprising an algal feed supplement comprising a minimum of 20% of aNDF by dry weight, a minimum of 16% protein by dry weight, a maximum of 3000 ppm iodine by dry weight, and a minimum of 2.5% bromoform by dry weight accompanied by instructions for supplementing the total mixed ration with about 6.5 g of product per kg of neutral dietary fiber (aNDF).

In another embodiment, the present technology provides for a kit comprising an algal feed supplement comprising a minimum of 20% of aNDF by dry weight, a minimum of 16% protein by dry weight, a maximum of 3000 ppm iodine by dry weight, and a minimum of 2.5% bromoform by dry weight accompanied by instructions for supplementing the total mixed ration from about 4.5 g to 8.5 g of product per kg of neutral dietary fiber (aNDF).

Enhanced Methane Producing Manure

In other embodiments, the compositions and methods of the present technology provide for the use of manure from *Asparagopsis* spp., *Asparagopsis taxiformis*, or a composition comprising *Asparagopsis taxiformis* brominata treated ruminants to produce methane using a manure digester to obtain improved yields of methane than those obtained from the manure of untreated cows.

In other embodiments, the compositions and methods of the present technology provide for the use of manure from *Asparagopsis* spp., *Asparagopsis taxiformis*, or a composition comprising *Asparagopsis taxiformis* brominata treated ruminants to produce methane using covered manure lagoon to obtain improved yields of methane than those obtained from the manure of untreated cows.

Manure Methane Remediation

While we have found that treating animals with the compositions and methods of the present technology reduces the amount of methane the animal belches, we have found surprisingly that the manure from such treated animals may produce more methane than the manure from untreated animals. Thus, the present technology also offers for either treating the manure itself with the algal biomass compositions described herein, other antimethanogenic compounds described herein, or combinations thereof. This method of treating the manure with the compositions and methods of the present technology may be performed on the manure from animals supplemented with the compositions and methods of the present technology or on the manure from untreated animals.

In some embodiments, the compositions and methods of the present technology provide for the treatment of ruminant manure with a composition comprising about 1 g/ton, 10 g/ton, 50 g/ton, 100 g/ton, 500 g/ton, 1 kg/ton, or 10 kg/ton of *Asparagopsis* spp., *Asparagopsis taxiformis*, or a composition comprising *Asparagopsis taxiformis* brominata.

In some embodiments, the compositions and methods of the present technology provide for the treatment of ruminant manure with a composition comprising about 1 g/ton, 10 g/ton, 50 g/ton, 100 g/ton, 500 g/ton, 1 kg/ton, or 10 kg/ton of bromoform, encapsulated bromoform, or a compound or element selected from the compounds or elements depicted in FIG. 2.

In other embodiments, the compositions and methods of the present technology provide for the use of manure from *Asparagopsis* spp., *Asparagopsis taxiformis*, or a composition comprising *Asparagopsis taxiformis* brominate treated ruminants to produce methane using a manure digester to obtain improved yields of methane than those obtained from the manure of untreated cows.

In other embodiments, the compositions and methods of the present technology provide for the use of manure from *Asparagopsis* spp., *Asparagopsis taxiformis*, or a composition comprising *Asparagopsis taxiformis* brominata treated ruminants to produce methane using covered manure lagoon to obtain improved yields of methane than those obtained from the manure of untreated cows.

In some embodiments, the composition used to treat the manure may comprise one or more compounds selected from the group consisting of: 3-nitrooxypropanol, Mootral (a product of Mootral, a Swiss Agritech company), garlic extract, Yucca extract, Yucca powder, saponin, furostanol aglycone, spirostanol aglycone, chloroform, sarsapogenin, markogenin, smilagenin, samogenin, gitogenin, neogito-genin, monodesmosidic saponins, YS-I, YS-II, YS-III, YS- IV, YS-V, YS-VI, YS-VII, YS-VIII, YS-IX, YS-X, YS-XI, YS-XII, YS-XIII, bidesmoside saponin components, monodesmoside saponin components, quillaya saponins, proanthocyanidins, condensed tannins, hydrolysable tannins, Gynosaponins powder, Tea saponin, *Sesbania sesban* leaves extract, *Acacia mearnsii* extract, *Acasia saligna* leaves, *Leucaena leucocephala* extracts, *Lespedeza striata* forage, Combination of essential oil (809 g/kg eugenol in thyme oil; 837 g/kg carvacrol in oregano oil; 855 g/kg cinnamaldehyde in cinnamon oil; 801 g/kg limonene in lemon oil) plus monosodium fumarate, Combination of essential oil (eugenol, carvacrol, citral, cinnamaldehyde; purity 0.99%) plus monosodium fumarate, Agolin Ruminant (Agolin S. A. Of Biere, Switzerland), and *Mentha microphylla* (piperitone oxide and cis-piperitone oxide—46.7% and 28%).

In some embodiments, the compositions and methods of the present technology provide for the treatment of ruminant manure with a composition comprising of one or more compounds selected from the group consisting of: 3-nitrooxypropanol, Mootral (a product of Mootral, a Swiss Agritech company), garlic extract, Yucca extract, Yucca powder, saponin, furostanol aglycone, spirostanol aglycone, chloroform, sarsapogenin, markogenin, smilagenin, samogenin, gitogenin, neogitogenin, monodesmosidic saponins, YS-I, YS-II, YS-III, YS-IV, YS-V, YS-VI, YS-VII, YS-VIII, YS-IX, YS-X, YS-XI, YS-XII, YS-XIII, bidesmoside saponin components, monodesmoside saponin components, quillaya saponins, proanthocyanidins, condensed tannins, hydrolysable tannins, Gynosaponins powder, Tea saponin, *Sesbania sesban* leaves extract, *Acacia mearnsii* extract, *Acasia saligna* leaves, *Leucaena leucocephala* extracts, *Lespedeza striata* forage, Combination of essential oil (809 g/kg eugenol in thyme oil; 837 g/kg carvacrol in oregano oil; 855 g/kg cinnamaldehyde in cinnamon oil; 801 g/kg limonene in lemon oil) plus monosodium fumarate, Combination of essential oil (eugenol, carvacrol, citral, cinnamaldehyde; purity 0.99%) plus monosodium fumarate, Agolin Ruminant (Agolin S. A. Of Biere, Switzerland), and *Mentha microphylla* (piperitone oxide and cis-piperitone oxide—46.7% and 28%) at a rate of about 1 g/ton, 10 g/ton, 50 g/ton, 100 g/ton, 500 g/ton, 1 kg/ton, or 10 kg/ton.

In some embodiments the composition used to treat the manure may comprise other methane-reducing, quality and quantity enhancing components as disclosed in A. Cieslak, M. Szumacher-Strabel, A. Stochmal and W. Oleszek, Animal (2013), 7: s2, pp 253-265 & The Animal Consortium 2013, doi: 10.1017/S1751731113000852, which is incorporated herein in its entirety.

In a preferred embodiment, the compositions of the present technology further comprise 3-nitrooxylpropanol (3-NOP).

In another preferred embodiment, the compositions of the present technology further comprise Agolin Ruminant (Agolin S. A. Of Biere, Switzerland).

In another preferred embodiment, the compositions of the present technology further comprise Agolin Ruminant (Agolin S. A. Of Biere, Switzerland) and 3-nitrooxylpropanol (3-NOP).

In another preferred embodiment, the methods of the present technology provide for the administration of Agolin Ruminant (Agolin S. A. Of Biere, Switzerland) in combination with a tetrasporophyte derived algal biomass to an animal.

In another preferred embodiment, the methods of the present technology provide for the administration of 3-nitrooxylpropanol (3-NOP). In combination with a tetraspo-rophyte derived algal biomass to an animal.

In another preferred embodiment, the methods of the present technology provide for the administration of 3-ni-trooxylpropanol (3-NOP) and Agolin Ruminant (Agolin S. A. Of Biere, Switzerland). In combination with a tetraspo-rophyte derived algal biomass to an animal.

In another preferred embodiment, the methods of the present technology provide for the treatment of manure with Agolin Ruminant (Agolin S. A. Of Biere, Switzerland) in combination with a tetrasporophyte or gametophyte derived algal biomass to an animal.

In another preferred embodiment, the methods of the present technology provide for the treatment of manure with 3-nitrooxylpropanol (3-NOP) in combination with a tet-rasporophyte or gametophyte derived algal biomass to an animal.

In another preferred embodiment, the methods of the present technology provide for the treatment of manure with Agolin Ruminant (Agolin S. A. Of Biere, Switzerland) and 3-nitrooxylpropanol (3-NOP) in combination with a tet-rasporophyte or gametophyte derived algal biomass to an animal.

In another preferred embodiment, the methods of the present technology provide for the treatment of manure with 3-nitrooxylpropanol (3-NOP).

In one embodiment, the present technology provides for the treatment of manure from animals not supplemented with the compositions and methods described herein.

Mineral Nutrient Requirements of Cattle

In some embodiments, the algal biomass provided to the ruminant animals is formulated into a feed supplement comprising further nutrient sources and excipients described below.

A beef cow requires energy, protein, minerals, and vita-mins in its diet. What determines how much of these nutrients is required? What determines if they need to be supplemented in the diet?

Many factors affect the amounts of required nutrients. A female performs many functions—body maintenance, activ-ity, weight gain, reproduction, and milk production—that all require nutrients. The amount of nutrients required depends on body size, environmental conditions, how far an animal travels, desired rate of gain, stage of gestation, and level of milk production.

The nutritional value and quantity of available forage determine if nutrients need to be supplemented in the diet. During most of the year, warm-season forages are likely to be deficient in some minerals, especially phosphorus and certain trace elements like copper and zinc. In most situa-tions, supplementation should include at least year-round provision of salt and a mineral with 8 percent to 12 percent phosphors and a similar level of calcium. Vitamin A, which usually is low in dry or weathered forages, should be injected or fed in mineral or other supplements if it is suspected to be deficient. Mineral and vitamin supplemen-tation should be a high priority because deficiencies can be corrected for relatively little cost.

After addressing mineral and vitamin needs, protein and energy deficiencies must be considered. Forage protein and energy vary seasonally. Warm-season forage typically becomes deficient in protein in mid-summer and again in winter. Forage lacks adequate energy content primarily in winter, but energy available to the animal is restricted more often by a limited supply of forage rather than by deficien-cies in plant composition.

Many factors affect the type and amount of protein or energy supplement that a beef cow may require. There are six critical factors that affect supplementation needs.

Forage Quantity. The amount of available forage obvi-ously affects the need for supplemental feed. If grazing or hay will be limited, take immediate action. Reduce the number of animals in order to lessen the need for supple-mental feeding of the remaining cows. As forage supply declines, the opportunity for animals to selectively graze decreases, and so does diet quality. Then, supplementation may become necessary even if animal numbers are reduced.

Forage Quality. Poor quality forage has less than 6 percent to 7 percent crude protein (CP) and is low in digestibility, with less than 50 percent total digestible nutrients (TDN). These deficiencies limit the amount of such forage that an animal can eat. Because both consumption and nutrient content of poor quality forage are low, supplemental needs are high. Medium quality forage (7 percent to 11 percent CP, 50 percent to 57 percent TDN) eliminates or significantly reduces the need for supplementation. High quality forage (above 12 percent to 14 percent CP and 57 percent TDN) can be consumed in the largest amounts and usually removes any need for supplementation, except possibly for high milking cows in low body condition. However, forage that is high in quality but low in quantity, a common situation in early spring, increases the need for supplementation of dietary bulk and energy. The amount a cow can eat in a day ranges from as little as 1.5 percent of body weight for very low quality forage to near 3.0 percent for very high quality forage. The typical amount is 2.0 percent to 2.5 percent.

Body Condition. The level of body condition (amount of fat) affects supplemental requirements. Low body condition markedly increases the need for supplemental nutrients, and meeting such needs often is cost prohibitive. Moderate body condition significantly reduces or eliminates the need for supplements. Fleshy cows generally need little if any supplement and the daily amount of forage required often can be reduced. If forage consumption is not reduced, higher production is possible or reserves of stored body energy can be maintained.

Body Size. The potential for forage consumption is related to body size, so larger animals may not require more supplement than smaller ones. Adjustments in stocking rate, to allow adequate amounts of forage per cow, may offset differences in size but will increase the cost per cow. But if forage is sparse or limited, larger cows require proportion-ately more supplement.

Milking Level. Higher milking cows can consume some-what more forage, but not enough to completely satisfy extra needs. When forage quality is inadequate, higher milking cows need more supplement; from 50 percent to 100 percent more may be required for high versus low milk production in cows of the same body size.

Age. Young animals are still growing and require extra nutrients, but their body size is not as large as mature animals. Because of their smaller body size, growing heifers cannot consume as much forage as mature cows. For these reasons, young females require higher quality diets than mature cows and often require more and different supple-ments.

The compositions and methods of the current technology can be used in conjunction with the below described supple-ment forms:

Oilseed Meals. Cottonseed, soybean, and peanut meals often are manufactured as large pellets or cubes for feeding convenience. These are high protein (38 percent to 45 percent CP), medium to high energy sources, commonly fed at 1 pound to 3 pounds a day. Although relatively costly per ton, they often are the cheapest source of protein. These feeds are most useful when supplemental protein, and little or no energy, is needed. Oilseed meals are especially suitable for dry cows in moderate to good flesh when they have access to adequate amounts of low protein, medium energy forages.

Grain. Corn and grain sorghum (milo) are the most comm on low protein, high energy sources. Other grains include oats, wheat, and barley. Grains often are the cheapest sources of supplemental energy. Similar feeds include processed by products such as wheat mids, soybean hulls, and rice bran. These by products are slightly higher in protein and a little lower in energy than grains and are relatively low in starch. Starch can interfere with forage digestibility, so these are excellent supplements to forage. Feeds in this category commonly are found in breeder/range cubes.

Breeder/Range Cubes. These are most commonly 20 percent CP but also are found as 30 percent to 32 percent products. These feeds are designed to provide a combination of protein and energy, fed in larger amounts (3 to 6 pounds a day) than high protein feeds. The equivalent of a 20 percent cube can be prepared with a mix of about one-third oilseed meal and two-thirds grain. A mix of about three-fourths meal and one-fourth grain is the equivalent of a 32 percent cube. Some cubes use nonprotein nitrogen (NPN), usually urea, to supply nitrogen for potential synthesis of rumen microbial protein. Cubes with low crude fiber (below 10 percent) generally are highest in energy. Whole cotton-seed, brewers grains, and some corn gluten meals are similar in protein and energy content to these cubes.

Protein Blocks and Liquids. These feeds usually contain 30 percent to 40 percent CP and typically are low to medium in energy. Their formulation or physical structure limits consumption to around 1 pound to 3 pound s daily. The protein portion often consists of 50 percent to 90 percent from NPN, but can be considerably lower. Their primary use is to provide supplemental protein on low protein, medium energy forages (below 7 percent CP, 50 percent to 52 percent TDN) where convenience of self-feeding is a priority. These feeds generally will not fill large voids of nutrient deficiency, nor support higher levels of animal performance.

Syrup Blocks and Tubs. These generally range from 12 percent to 24 percent CP (often about half from NPN) and are medium in energy. Consumption of these blocks usually is very low (typically ½ pound to 1½ pounds a day), so higher protein versions probably are most useful. These products are not intended to directly supply much supplemental protein or energy. Rather, their theoretical function is to stimulate rumen microbes to digest more forage and produce microbial protein, which can be utilized in the small intestine. For this to occur, sufficient amounts of at least moderately digestible forage must be available. These feeds work best when supplied year round, allowing accumulation of body fat reserves that animals can utilize during typical fall and winter decline in forage quality and quantity. They generally will not support high performance.

Hays. High quality hays, such as alfalfa, peanut, and soybean, can be used as supplements. These medium protein (usually 15 percent to 20 percent CP), medium energy sources can be limit-fed in place of one of the feeds discussed previously. Such hays also can be fed free choice, although protein is wasted, if their cost is competitive.

Supplements must be chosen to meet particular nutrient deficiencies. Body condition is a key factor in the choice of supplements. Thin cows are relatively more deficient in dietary energy than in protein. In contrast, fleshier cows may need extra protein, if they need anything. To minimize supplementation, use forage supplies logically. In general, hay (excluding supplemental alfalfa, etc.) should not be limit-fed with standing forage. Limit-feeding of hay encourages cows to reduce grazing and fails to use pastures while quality is reasonably good. For example, assume available forage for grazing or feeding includes some tame pasture (such as coastal bermudagrass), some native range, and some hay. As winter approaches, the tame pasture should be used first, native range next, and hay last. That way each forage is utilized most efficiently, and there is a better chance some hay will be left in late winter to early spring when high quality green growth begins but is limited in amount.

In certain embodiment, the compositions and methods of the present technology provide for animal supplements and animal supplementation methods that inhibit methane production in ruminants and do not require any changes in the typical supplementation regimes described below.

In other embodiments, the compositions and methods of the present technology provide for animal supplements and animal supplementation methods that inhibit methane production in ruminants and include the appropriate mineral supplements as part of the methane inhibiting formulation.

It is difficult to make general recommendations about supplementation of protein and energy. Usually, dry mature cows in medium or higher body condition on typical dormant warm-season pasture or low-quality hay often need only 1 pound to 2 pounds a day of a high protein feed. (On extremely low-quality forage, such as tall-grass prairie in winter, 3 pounds to 4 pounds of high protein feed may be needed.) A thin, dry, mature cow may require 2 pounds to 4 pounds daily, but of a medium-protein, high-energy supplement. After calving, all of these amounts essentially should be doubled.

Daily feeding usually is not necessary when using high-protein supplements such as cottonseed meal cubes. Instead, depending on the amounts, weekly required totals can be divided and fed every other day, twice a week, or even once a week. In fact, nondaily feeding of these supplements often is more efficient. However, combination protein-energy supplements, especially breeder/range cubes and meal-grain mixes, that are required in larger daily amounts, generally should be fed daily for best forage utilization, highest animal performance, and greatest efficiency.

Self-fed, controlled consumption can be accomplished with some feeds, especially oilseed meals and meal-grain mixes, by including an intake limiter such as salt. Cattle then will consume salt in maximum amounts of approximately 0.1 percent of body weight, or about 1 pound of salt consumption daily by a 1,000-pound cow. So, to obtain supplement consumption of 3 pounds daily in a 1,000-pound cow, a mix of 1 pound salt to 3 pounds supplement should be provided. When using salt to limit consumption, plenty of high quality water must be available. Also, cows consume more of a salt-limited supplement when it is located close to a water supply.

Perhaps the most common supplement is a high quality 20 percent CP breeder/range cube (high or all-natural protein and low crude fiber), or the equivalent. Such a supplement often is a compromise for the common situation of low quality forage and low to medium body condition. But this must be fed in adequate amounts, typically 3 to 6 pounds a day, to be effective. In fact, with the exception of managing weight loss in fleshy cows, there are few situations where feeding smaller amounts of such cubes is applicable. If a producer is unwilling or unable to assume the cost of required amounts of these cubes (or the equivalent), then a lower amount of a higher protein feed should be fed. But realize, however, that body condition, reproduction, productivity, and profit are likely to decline if nutrient requirements are not met.

Minerals and vitamins account for a very small proportion of daily dry matter intake in beef cattle diets and can sometimes be overlooked in a herd nutritional program. Although minerals and vitamins are needed as a very small percentage of dietary nutrients, they are very important in beef cattle nutritional programs for proper animal function, such as bone development, immune function, muscle contractions, and nervous system function. Cattle growth and reproductive performance can be compromised if a good mineral program is not in place. A good mineral and vitamin supplementation program costs approximately $15 to $25 per head per year. With annual cost of production per cow generally being several hundred dollars, the cost of a high-quality mineral and vitamin supplement program is a relatively small investment. Many free-choice mineral and vitamin mixes are formulated for 2- or 4-ounce daily consumption rates. For illustration purposes, if a beef cow consumes 4 ounces (¼ pound) of a supplement per day for 365 days, then she consumes 91.25 pounds of the supplement in a year. Many mineral and vitamin supplements are packaged in 50-pound bags, so a beef cow consumes almost two 50-pound bags of this supplement annually at the 4-ounce daily consumption rate. Doubling the price of one of these bags of mineral and vitamin supplement approximates the annual cost of the supplement on a per-head basis.

Beef cattle require at least 17 different mineral elements in their diets. Required minerals are classified as either macrominerals (major minerals) or microminerals (trace minerals), based on the quantities required in beef cattle diets. Macrominerals are required in larger quantities (grams per day) than microminerals (milligrams or micrograms per day).

Macrominerals required by beef cattle include calcium, magnesium, phosphorus, potassium, sodium, chlorine, and sulfur. Required microminerals include chromium, cobalt, copper, iodine, iron, manganese, molybdenum, nickel, selenium, and zinc. Nutrient requirements of specific mineral elements vary, depending on animal age, weight, stage of production, lactation status, breed, stress, and mineral bioavailability (the degree to which a mineral becomes available to the target tissue after administration) from the diet.

Macromineral requirements are typically expressed as a percentage (%) of the total diet, while micromineral requirements are generally expressed as milligrams per kilogram (mg/kg), which is the equivalent of parts per million (ppm). To convert percent to ppm, move the decimal four places to the right (for example 0.2500%=2500 ppm). Dietary mineral sources include forages, concentrate feedstuffs, mineral supplements, and water.

Minerals interact with each other in the body. The many interactions can result in mineral elements' tying up or making other mineral elements unavailable for essential body functions. In practical beef cattle nutrition programs, the interaction between calcium and phosphorus is the classic example of two minerals that affect the required levels of each other in the diet. Calcium and phosphorus recommendations are commonly expressed as a ratio (Ca:P) of calcium to phosphorus.

Cattle can tolerate high concentrations of dietary calcium if other mineral levels are adequate in the diet. Calcium recommendations are expressed in terms of a calcium to phosphorus ratio (Ca:P), where approximately 1.6:1 is ideal, with a range of 1:1 to 4:1 being acceptable. Supplemental calcium sources include calcium carbonate, feed-grade limestone, dicalcium phosphate, defluorinated phosphate, monocalcium phosphate, and calcium sulfate. Feed-grade limestone is approximately 34 percent calcium and is commonly added to beef cattle diets to increase the calcium levels of the diet. Dicalcium phosphate is approximately 22 percent calcium and 19.3 percent phosphorus and is added to beef cattle diets to help balance the calcium to phosphorus ratio. It adds both calcium and phosphorus to the diet. Recommended phosphorus levels in a mineral supplement are generally from 4 to 8 percent, largely depending on forage conditions and other levels of dietary sources of phosphorus.

Encapsulation

The concentrations of Bromoform and other halogenated compounds present in *Asparagopsis taxiformis* and other algae, micro algae, macroalgae, and red macroalgae vary widely based on the growth environment, seasonality, species strain and other known and unknown factors, making the use of compositions derived from such algae biomass difficult to produce on a consistent basis and thus difficult to commercialize in a heavily regulated marketplace.

In vitro and in vivo testing has identified a strong positive correlation between the level of methane reduction in ruminants and the ratio of the bromoform component delivered from a red macroalgae feed supplement, relative to specific components of the animal's diet.

Additional in vivo testing has discovered that bromoform delivered from a red macroalgae feed supplement is degraded in livestock rumens in such a way that bromoform is not absorbed into the rumen wall, or other organs, and it is not found in metabolic byproducts produced by livestock, such as their milk, meat, or manure.

Bromoform may be artificially synthesized by several methods, including a haloform reaction using acetone and sodium hypobromite, electrolysis of potassium bromide in ethanol, or by treating chloroform with aluminum bromide. Thus, there is a need for a new and useful system and method that artificially synthesizes and encapsulates bromoform in ways that are cost-efficient, safe to livestock and the environment, and effective when fed to livestock. This invention provides such a new and useful system and method.

In various aspects, the present technology solves the problem of having to build and maintain large-scale algaculture installations and the issues of excess iodine ingestion by animals and people who consume their products by providing compositions, and methods for making those compositions of target component infused feed products or target component feed supplements.

In certain embodiments, the compositions and methods of the present technology provide for encapsulated bromoform composition comprising a bromoform bearing core and an edible polymeric material that forms an encapsulation barrier.

In certain embodiments, the encapsulation material forming the encapsulation barrier is an edible polymeric material and may be selected from, for example, polymers; resins; carbohydrates; modified carbohydrates; mono-, di-, oligo- or poly-saccharides; starches; modified starches; proteins; fatty acids; polyglycerol fatty acid esters; acrylics; vegetable gums; polyvinyl acetate; polyvinylpyrrolidone; poly(1-vinylpyrrolidone-co-vinyl acetate); povidone; crospovidone; Kollidon® polymers; Kollidon®-CL; Kollidon®-25; Kollidon®-30; Kollidon®-90; Kollidon®-12 PF; Kollidon®-17 PF; Kollidon®-VA 64; Aquacoat® aqueous dispersions; halocarbons; Aquateric® enteric coatings; hydrocarbon resins; polyvinyl alcohol; cellulose acetate; hydroxyl propyl cellulose (HPC); polyvinyl chloride; cellulose acetate butyrate; hydroxy propyl methyl cellulose (HPMC); poly-vinylacetate phthalate; cellulose acetate phthalate; hydroxy propyl methyl cellulose phthalate; polyvinylidene chloride; caseinates; Kynar® fluoroplastics; chlorinated rubber; maltodextrins; rubber; synthetic; Coateric® coatings; Opa-glos® coating systems; Opaglos®-GS-2-0400; Opaglos®-GS-2-0450; Opaglos®-GS-2-0700; Opaglos®-GS-2-0750; Opadry®; alkyl celluloses such as methyl cellulose and ethyl cellulose; shellac; coating butters; microcrystalline wax; silicone; Daran® latex; milk solids; dextrins; molasses; stearines; nylon; sucrose; enterics; surfactants; Eudragits® polymethacrylates; paraffin wax; Surelease® coating systems; ethylene vinyl acetate; phenolics; Teflon® fluorocarbons; fats; polylactides; polyglycolides; waxes; amino acids; polyamino acids; zein; Aqua-Zein®; gelatin; polyethylene; polyethyleneoxide; glycerides; polyethylene glycol; whey protein isolate; or combinations thereof.

In other embodiments, the encapsulation barrier may comprise other additives such as, but not limited to: dextrose, dextrin, gum arabic, guar gum, maltose, sucrose, pectin, hydroxyl propyl cellulose (HPC), hydroxypropyl methyl cellulose (HPMC), methylcellulose, Eudragit® polymers (polyacrylates and methyacrylic acid-ethyl acrylate copolymers), Carbowax™ Sentry™ polyethylene glycol (e.g., PEG-8000), Sentry™ Polyox™ WSR N12K-NF Grade, Sentry™ Polyox™ WSR 301-NF Grade, water-soluble shellacs (preferably refined food-grade confectioners glaze), starch, modified starches, sodium chloride, alanine, arginine, asparagines, aspartic acid, cysteine, glutamine, glutamic acid, glycine, histidine, isoleucine, leucine, lysine, methionine, phenylalanine, proline, serine, threonine, tryptophan, tyrosine, valine, guar gum, sugars, sweeteners, lecithin, sodium dodecyl sulfate, Tween-20, Tween-60, Tween-85, Lutrol® systems, sodium phosphate monobasic, tartaric acid, aspartic acid, ascorbic acid, castor oil, vegetable oils, fatty acids, and glyceryl monostearate.

In still other embodiments, the bromoform bearing core may further comprise: dextrose, dextrin, gum arabic, guar gum, maltose, sucrose, pectin, hydroxyl propyl cellulose (HPC), hydroxypropyl methyl cellulose (HPMC), methyl-cellulose, Eudragit® polymers (polyacrylates and methyacrylic acid-ethyl acrylate copolymers), Carbowax™ Sentry™ polyethylene glycol (e.g., PEG-8000), Sentry™ Polyox™ WSR N12K-NF Grade, Sentry™ Polyox™ WSR 301-NF Grade, water-soluble shellacs (preferably refined food-grade confectioners glaze), starch, modified starches, sodium chloride, alanine, arginine, asparagines, aspartic acid, cysteine, glutamine, glutamic acid, glycine, histidine, isoleucine, leucine, lysine, methionine, phenylalanine, proline, serine, threonine, tryptophan, tyrosine, valine, guar gum, sugars, sweeteners, lecithin, sodium dodecyl sulfate, Tween-20, Tween-60, Tween-85, Lutrol® systems, sodium phosphate monobasic, tartaric acid, aspartic acid, ascorbic acid, castor oil, vegetable oils, fatty acids, and glyceryl monostearate.

In still other embodiments, the encapsulation barrier may further comprise, or be coated with sweetners such as, but not limited to: sucrose, L-aspartyl-L-phenylalanine methyl ester, sorbitol, xylitol, and mannitol, fructose, molasses, beet sugar, brown sugar, cane sugar, confectioner's sugar, powdered sugar, raw sugar, turbinado, maple syrup, carob powder, corn syrup, sugar cane syrup, honey, sweetened condensed milk, and chocolate, saccharin, aspartame, acesulfame potassium, sucralose, and stevia.

In other embodiments, the encapsulation barrier may comprise other additives such as, but not limited to:

Advanta-Gel™ P75, Batter Bind® S, Crisp Coat UC, Crisp Film®, Crystal Gum, Crystal TeX™ 627, Crystal Tex™ 644, Crystal Tex™ 648, Elastigel™ 1000J, Encapsul 855, Flojel® 60, Flojel® 65, Flojel® G, Hi-Set® 322, Hi-Set® 377, Hi-Set® C, Hi-Set® CHG, Hylon® V, Hylon® VII, Impression™, K4484, Melojel®, Nadex™ 772, National 0280, National 814, N-TACK®, Purity® 21D, Purity® TF, Superset® LV, Ultra-Set® LT, Dry-Tack® 250, Versa-Sheen™, Baka-Plus™, Baka-Snak®, Capsul®, Capsul® TA, Gel N Melt®, H-50, Hi-Cap™ 100, Hi-Cap™ 200, IF 131, Instant ClearGel®, Instant Pure-Flo, Instant Pure-Flo F, Instant Textaid-A, Instant Textra, National 104, National 1215, National 46, National 1517, National 5730, National 711, National 78-1551, N-Creamer 46, N-Flate, N-Lite™ LP, N-LOK®, N-LOK® 1930, Novation® 4600, Novation® 5600, Novation® 9460, Purity Gum 1773, Purity Gum 2000, Purity Gum 539, Purity Gum BE, Purity® HO, Stir-N-Set® FG, Text-Aid-A®, Textra® Plus, Ultra-Crisp CS, Ultra-Sperse® 2000, Ultra-Sperse® 5, Ultra-Sperse® A, Ultra-Sperse® M, Ultra-Tex 1, Ultra-Tex 2, Ultra-Tex 2000, Ultra-Tex 3, Ultra-Tex 4, AbsorboHP, Amioca, Can-Fil®, Dry-Flo, Hoosier 5, National 150, National 1545, National 6912, National 77-1744, National 912, N-Zorbit® M, Purity® 21, Purity® 5, Purity® 825, Purity® 826, Purity® FC, Target brand tapioca, NU Mould™, Purity® 5S, Clearjel®, Clearjel® S, Colflo® 67, Firm-Tex®, Frigex® w, Hi FLO®, National 1333, National 1457, National 1658, National 4012, National 465, National 740, National Frigex, National Frigex HV, National® 320, Novation® 1600, Novation® 1900, Novation® 2300, Novation® 2600, Novation® 2700, Novation® 3300, Novation® 3600, Novation® 9230, Novation® 9260, Novation® 9270, Novation® 9330, Novation® 9360, Pure-Flo®, Purity® 270, Purity® 4, Purity® 420, Purity® 550, Purity® 660, Purity® 69, Purity® 87, Purity® Cloud, Purity® CSC, Purity® D, Purity® HPC, Purity® W, Thermflo®, Thermtex®, WNA. In still other embodiments, the bromoform bearing core may further comprise: Advanta-Gel™ P75, Batter Bind® S, Crisp Coat UC, Crisp Film®, Crystal Gum, Crystal TeX™ 627, Crystal Tex™ 644, Crystal Tex™ 648, Elastigel™ 1000J, Encapsul 855, Flojel® 60, Flojel® 65, Flojel® G, Hi-Set® 322, Hi-Set® 377, Hi-Set® C, Hi-Set® CHG, Hylon® V, Hylon® VII, Impression™, K4484, Melojel®, Nadex™ 772, National 0280, National 814, N-TACK®, Purity® 21D, Purity® TF, Superset® LV, Ultra-Set® LT, Dry-Tack® 250, Versa-Sheen™, Baka-Plus™, Baka-Snak®, Capsul®, Capsul® TA, Gel N Melt®, H-50, Hi-Cap™ 100, Hi-Cap™ 200, IF 131, Instant ClearGel®, Instant Pure-Flo, Instant Pure-Flo F, Instant Textaid-A, Instant Textra, National 104, National 1215, National 46, National 1517, National 5730, National 711, National 78-1551, N-Creamer 46, N-Flate, N-Lite™ LP, N-LOK®, N-LOK® 1930, Novation® 4600, Novation® 5600, Novation® 9460, Purity Gum 1773, Purity Gum 2000, Purity Gum 539, Purity Gum BE, Purity® HO, Stir-N-Set® FG, Text-Aid-AR, Textra® Plus, Ultra-Crisp CS, Ultra-Sperse® 2000, Ultra-Sperse® 5, Ultra-Sperse® A, Ultra-Sperse® M, Ultra-Tex 1, Ultra-Tex 2, Ultra-Tex 2000, Ultra-Tex 3, Ultra-Tex 4, AbsorboHP, Amioca, Can-Fil®, Dry-Flo, Hoosier 5, National 150, National 1545, National 6912, National 77-1744, National 912, N-Zorbit® M, Purity® 21, Purity® 5, Purity® 825, Purity® 826, Purity® FC, Target brand tapioca, NU Mould™, Purity® 5S, Clearjel®, Clearjel® S, Colflo® 67, Firm-Tex®, Frigex® w, Hi FLO®, National 1333, National 1457, National 1658, National 4012, National 465, National 740, National Frigex, National Frigex HV, National® 320, Novation® 1600, Novation®

1900, Novation® 2300, Novation® 2600, Novation® 2700, Novation® 3300, Novation® 3600, Novation® 9230, Novation® 9260, Novation® 9270, Novation® 9330, Novation® 9360, Pure-Flo®, Purity® 270, Purity® 4, Purity® 420, Purity® 550, Purity® 660, Purity® 69, Purity® 87, Purity® Cloud, Purity® CSC, Purity® D, Purity® HPC, Purity® W, Thermflo®, Thermtex®, WNA.

The microcapsules of the invention are prepared by (i) dissolving the edible encapsulation material (e.g., polymeric or resin) in a suitable organic solvent; (ii) mixing the solubilized encapsulation material with a core material comprising bromoform adsorbed or absorbed on a carrier material, slowly adding to the mixture, with stirring, a nonsolvent for the encapsulation material. This gives microcapsules or microparticles with a core material comprising an acid, a base, effervescent couples, and/or combinations of these components, coated with a permeable encapsulation barrier comprising a water-insoluble edible organic polymeric material that is optionally water-swellable. The terms "slowly adding" and "slow addition" refer herein to the speed of addition which results in the even distribution of encapsulation material onto the core material. Such speed of addition can be determined without undue experimentation by those skilled in the art.

Examples of suitable solvents and non-solvents include, but are not limited to: acetic acid, acetone, acetonitrile, acetyl acetone, acrolein, acrylonitrile, allyl alcohol, 1,3-butanediol, 1,4-butanediol, 1-butanol, 2-butanol, tert-butanol, 2-butoxyethanol, n-butyl amine, butyl dioxitol acetate, butyraldehyde, butyric acid, 2-chloroethanol, decane, diacetone alcohol, diacetyl, diethylamine, diethylene glycol diethyl ether, diethylene glycol dimethyl ether, diethylene glycol monobutyl ether, diethylene glycol monobutyl ether acetate, diethylene glycol monoethyl ether, diethylene glycol monoethyl ether acetate, diethylene glycol monomethyl ether, N,N-diethylnicotinamide, diethyl ether, dimethyl sulfoxide, N,N-dimethylacetamide, N,N-dimethylformamide, 1,4-dioxane, ethanol, 2-ethoxyethanol, 2-ethoxyethyl acetate, ethyl acetate, ethyl formate, ethylene glycol methyl ether acetate, formic acid, furfural, glycofurol, hexane, hexanes, hexylene glycol, isobutanol, isopropyl alcohol, 2,6-lutidine, methanol, methyl acetate, methyl ethyl ketone, methyl isopropyl ketone, methyl propionate, N-methylpyrrolidone, morpholine, nonane, pentane, pentanes, tert-pentanol, 2-picoline, 3-picoline, 4-picoline, piperidine, 1-propanol, 2-propanol, propionaldehyde, propylene oxide, pyridine, pyrimidine, pyrrolidine, tetrahydrofuran, tetramethylurea, triacetin, triethylene glycol, supercritical carbon dioxide, trimethyl phosphate, acetic acid isopropyl ester (isopropyl acetate), acetic acid sec-butyl ester, acetophenone, n-amyl acetate, aniline, benzaldehyde, benzene, benzophenone, benzyl alcohol, benzyl amine, benzyl benzoate, bromobenzene, bromoform, n-butyl acetate, butyric acid methyl ester, caproic acid, carbon disulfide, carbon tetrachloride, o-chloroaniline, chlorobenzene, 1-chlorobutane, chloroform, chloromethane, m-chlorophenol, m-cresol, o-cresol, cyanoethane, cyanopropane, cyclohexanol, cyclohexanone, 1,2-dibromoethane, dibromomethane, dibutyl amine, m-dichlorobenzene, o-dichlorobenzene, 1,1-dichloroethane, 1,2-dichloroethane, dichlorofluoromethane, diethyl carbonate, diethyl malonate, diethyl sulfide, diethylene glycol dibutyl ether, diisobutyl ketone, diisopropyl sulfide, dimethyl phthalate, dimethyl sulfate, dimethyl sulfide, N,N-dimethylaniline, enanthic acid, ethyl acetoacetate, ethyl benzoate, ethyl propionate, ethylbenzene, ethylene glycol monobutyl ether acetate, exxate 600, exxate 800, exxate 900, fluorobenzene, furan, hexamethylphosphoramide, 1-hexanol, n-hexyl acetate, isoamyl alcohol (3-methyl-1-butanol), isobutyl acetate, methoxybenzene, methyl amyl ketone, methyl benzoate, methyl formate, methyl isoamyl ketone, methyl isobutenyl ketone, methyl isobutyl ketone, methyl n-butyl ketone, methyl propyl ketone, 4-methyl-2-pentanol, N-methylaniline, methylene chloride, nitrobenzene, nitroethane, 1-nitropropane, 2-nitropropane, 1-octanol, 2-octanol, 1-pentanol, 3-pentanone, 2-phenylethanol, n-propyl acetate, quinoline, styrene, 1,1,2,2-tetrachloroethane, 1,1,2,2-tetrachloroethylene, toluene, 1,1,1-trichloroethane, 1,1,2-trichloroethane, 1,1,2-trichloroethylene, trifluoromethane, valeric acid, m-xylene, o-xylene, p-xylene, 2,4-xylenol or any combination of the above.

Suitable carriers include, but are not limited to, kaolin, silica, polyethylene glycol, clay nanoparticles, magnesium stearate, silica gel, surface derivatized silica, fumed silica, hectorite, colloidal magnesium-aluminum silicate, magnesium trisilicate, aluminum hydroxide, activated charcoal, talc, Neusilin, calcium silicate, magnesium oxide, zinc oxide, microcrystalline cellulose, croscarmellose sodium, and polymethacrylate.

Described herein are systems and methods that artificially synthesize and encapsulate bromoform in a way that is safe for livestock to consume, safe for the environment, and effective in reducing livestock enteric methane emissions as well as increasing the quantity and quality of the products derived from such livestock.

The components of these systems include methods that artificially synthesize bromoform and methods that encapsulate artificially synthesized bromoform. In one embodiment, a chemical reaction is used to synthesize bromoform. In a further embodiment, this chemical reaction occurs in specific and controlled environmental conditions. In one embodiment, bromoform is encapsulated by a coating material. In one embodiment, bromoform is embedded in a homogeneous or heterogeneous matrix. In further embodiments, the method of encapsulation of the present technology prevents bromoform from volatizing, or chemically reacting to environmental conditions prior to digestion in livestock rumens.

In further embodiments, the method of encapsulation of the present technology allows bromoform to react with common enzymes in livestock rumens thereby causing the bromoform to degrade safely and usefully.

In another embodiment, biological methods are used to synthesize and encapsulate bromoform.

In one embodiment, a genetic screen is used to identify genes related to the synthesis and glandular encapsulation of bromoform in red macroalgae. In some implementations of this embodiment, genetic screens may include methods of forward genetic screens or methods of reverse genetic screens.

In one embodiment, genes related to the synthesis and glandular encapsulation of bromoform in red macroalgae are isolated and copied using recombinant DNA methods. In another embodiment, genes related to the synthesis and glandular encapsulation of bromoform in red macroalgae are copied by methods that artificially synthesize DNA.

In one embodiment, organisms which are capable of hosting genes related to the synthesis and glandular encapsulation of bromoform are identified and selected. In further embodiments, host organisms are identified and selected according to their ability to produce encapsulated bromoform in a production or manufacturing system.

In one embodiment, genes related to the synthesis and glandular encapsulation of bromoform are inserted into the DNA of a host organism using a vector. In some embodiments, insertion results in a transgenic host organism. In other embodiments, insertion results in a genetically edited host organism. In further embodiments, inserted genetic material is replicated by the host organism. In other embodiments, inserted genetic material is expressed by the host organism.

In one embodiment, organisms which contain the genes in red macroalgae that synthesize and encapsulate bromoform are propagated or cultivated in a unique growing medium. In further embodiments, these organisms produce encapsulated bromoform which are harvested. In further embodiments, this method of synthesis and encapsulation prevents bromoform from volatizing, or chemically reacting to environmental conditions prior to digestion in livestock rumens. In further embodiments, this method of synthesis and encapsulation allows bromoform to react with common enzymes in livestock rumens thereby causing the bromoform to safely and usefully degrade.

Shown in FIG. 11 is an embodiment of a system (1) in which a chemical reaction involving one or more chemicals or reagents (11) is introduced to one or more other chemicals or reagents (12) in the context of specific and controlled environmental conditions (13) to result in the chemical formation of bromoform $CHBr_3$ (14). Once formed, the bromoform is encapsulated by either a coating material (15) or is embedded in or encapsulated by a homogeneous or heterogeneous matrix (16).

Shown in FIG. 11 is an embodiment of a system (2) in which biological methods are used to synthesize and encapsulate bromoform. The system includes a method to identify (21) and isolate (22) genes related to the synthesis and glandular encapsulation of bromoform in red macroalgae. After these genes are identified and isolated, a method is used to copy them (23). Once copied, a vector (24) is used to insert the genes into the DNA of a host organism (25). The host organism is then propagated and cultivated in a unique medium (26). The result of the system (2) is bromoform which is encapsulated in a safe and useful way (27).

Surprisingly, the methods described in PCT application WO2017100062, incorporated herein by reference, that were developed for cannabinoids, vitamins, NSAIDS and vitamins are found useful for formulating very distinct, highly volatile target compounds such as bromoform. Also surprisingly, methods described in U.S. Pat. No. 5,989,583, incorporated herein by reference, are found to be useful for formulating the target compounds of the present invention as well.

Oral administration constitutes the preferred route of administration for a majority of target components, such as bromoform. However, target components that have an undesirable or bitter taste leads to lack of patient compliance in the case of orally administered dosage forms. In such cases, taste masking is an essential tool to improve patient compliance. Because target components (e.g., bromoform) may have an undesirable taste profile, in order to improve compliance, the presently disclosed compositions also comprise one or more target component taste masking agents. Examples of target components taste-masking agents include dry milk as described above, as well as menthol, sweeteners, sodium bicarbonate, ion-exchange resins, cyclodextrin inclusion compounds, adsorbates, and the like.

In some aspects, within the compositions and methods of the present technology, the formulation agent is an edible oil or fat, a protective colloid, or both a protective colloid and an edible oil or fat. In another aspect, the bioavailability enhancing agent is also a lipophilic active agent taste masking agent.

Examples of protective colloids include, but are not limited to, polypeptides (such as gelatin, casein, and caseinate), polysaccharides (such as starch, dextrin, dextran, pectin, and gum arabic), as well as whole milk, skimmed milk, milk powder or mixtures of these. However, it is also possible to use polyvinyl alcohol, vinyl polymers, for example polyvinylpyrrolidone, (meth)acrylic acid polymers and copolymers, methylcellulose, carboxymethylcellulose, hydroxypropylcellulose, cyclodextrins and alginates.

In other aspects, the bioavailability of the target component in a subject is at least about 1.5 times, about 2 times, about 2.5 times, about 3 times, about 3.5 times, about 4 times, about 4.5 times, about 5 times, about 5.5 times, about 6 times, about 6.5 times, about 7 times, about 7.5 times, about 8 times, about 8.5 times, about 9 times, about 9.5 times, or about 10 times greater than the bioavailability of the target component agent in the methanogenic organisms in the absence of the bioavailability enhancing agent.

As used herein, the term "bioavailability", bioavailability refers to the bioavailability of the target component to the methanogenic and other symbiotic organisms that colonize the rumen of ruminant animals, and not the bioavailability of the target components to the subject animal itself. This distinction is thought to be undesirable to expose the inner tissues of the animal to the target components, as this diminishes the amount of target component available to affect the methanogenic organisms as well as subjecting the subject animal to undesirable effects of the target components.

The target components of the present technology are effective over a wide dosage range. For example, in treating animals, compositions and methods of the present technology comprise dosages of target components ranging from about 0.01 mg to about 1,000 mg, from about 0.5 mg to about 500 mg, from about 1 mg to about 100 mg, from about 5 mg to about 50 mg, and about from 10 mg to about 25 mg.

Alternatively, in treating animals, compositions and methods of the present technology comprise dosages of target components of about 0.01 mg, about 0.05 mg, about 0.1 mg, about 0.25 mg, about 0.5 mg, about 0.75 mg, about 1 mg, 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1,000 mg.

Alternatively, in treating animals, compositions and methods of the present technology comprise dosages of target components of about 1500 mg, about 2000 mg, about 2500 mg, about 3000 mg, about 3500 mg, about 4000 mg, about 4500 mg, about 5000 mg, about 5500 mg, about 6000 mg, about 6500 mg, about 7000 mg, about 7500 mg, about 8000 mg, about 8500 mg, about 9000 mg, about 9500 mg, or about 10,000 mg.

Alternatively, in treating animals, compositions and methods of the present technology comprise dosages of target components of about 15,000 mg, about 20,000 mg, about 25,000 mg, about 30,000 mg, about 35,000 mg, about 40,000 mg, about 45,000 mg, about 50,000 mg, about 55,000 mg, about 60,000 mg, about 6,5000 mg, about 70,000 mg, about 7,5000 mg, about 80,000 mg, about 85,000 mg, about 90,000 mg, about 95,000 mg, or about 100,000 mg.

In some embodiments, the present technology is directed to dry solid lipid compositions useful for the oral delivery of lipophilic substances, and to methods for preparing and using such compositions.

In one aspect, the present technology provides for dry solid lipid mixtures that include a first component of a target component in an amount sufficient to provide a therapeutic effect when administered to an animal; a second component of a lipid comprising at least one solid fat; and a third component of at least one phospholipid, wherein the second and third components are present in an amount sufficient to increase the oral availability of the lipophilic substance when administered to the animal.

According to some embodiments of the present technology, the dry solid lipid mixtures may include one or more of an antioxidant, a cryoprotectant or a free-flow imparting agent.

The dry solid lipid mixtures of the present technology have shown unexpectedly high target component-loading efficiency and enhanced oral bioavailability for the target components.

In some further embodiments, the present technology further relates to methods for producing such dry solid lipid mixture compositions by dissolving the lipophilic substance together with lipid components comprising at least one solid fat and at least one phospholipid in a suitable organic solvent; evaporating the solvent to dryness; hydrating the dry solid lipid mixture with an aqueous phase, with mechanical shaking, to obtain a lipid dispersion in water; homogenizing the resultant lipid dispersion, such as by high-pressure homogenization, to reduce the particle size to the submicron range; and drying the submicron dispersion.

According to another embodiment, the dry solid lipid mixtures according to the present technology may be prepared by directly drying the lipid mixture that is dissolved in the organic solvent. For example, the solid lipid mixture formulations can be spray dried or freeze-dried to obtain dry compositions suitable for the preparation of solid-dosage forms, such as hard gelatin capsules or tablets. These solid dosage forms may further comprise cryoprotectants, antioxidants, free flowing imparting agents, surface active materials and/or emulsifiers.

These lipid compositions are suitable for the oral delivery of target components of methane reducing and animal product quality enhancing additives.

In some embodiments, the present technology is directed to dry solid lipid compositions for the oral delivery of lipophilic substances, and to methods for preparing and using such compositions.

In some aspects, the dry solid lipid mixtures of the present technology are composed of: i) a lipophilic substance, ii) a lipid or lipid mixture comprising at least one solid fat, and iii) one or more phospholipids. The dry lipid mixtures of the present technology, may further comprise an antioxidant, a cryoprotectant and/or a free-flow imparting agent.

Any of a wide variety of target components in addition to bromoform can be utilized in these mixtures. Examples include, but are not limited to: lipophilic drugs, vitamins, and hormones. These lipophilic substances include steroids, steroid antagonists, non-steroidal anti-inflammatory agents, antifungal agents, antibacterial agents, antiviral agents, anti-cancer agents, anti-hypertensives, anti-oxidants, anti-epileptic agents and antidepressants among many others. Additional examples of lipophilic drugs with very poor water solubility and low oral bioavailability which could benefit from oral dosage forms are the neurohormone melatonin, the antifungal agent amphotericin B, the anticancer drug etoposide, as well as tamoxifen and its analogs. More specific compounds include cannabinoids, as exemplified by dexanabinol, and vitamins, enzymes or coenzymes, as exemplified by CoQ10. Some lipophilic substances are those which have a water solubility of <200 µg/ml in water at room temperature (25° C.), and others <50 µg/ml.

The content of the lipophilic substance in the final dry solid lipid mixture may range from between about 0.01% and about 50% of the total solid weight of the mixture, or between about 5% and about 40% of the total solid weight of the mixture, or between about 7% and about 30% of the total solid weight of the mixture.

In the following description and claims, the term "solid fat" denotes any lipid or mixture of lipids, provided that the melting characteristics of the lipid or mixture are such that they exhibit a solid or liquid crystal phase at about 25° C.

Triglycerides which are solid at room temperature may be used in the preparation of the lipid mixture. The solid triglycerides may be composed of a single pure triglyceride, usually available as a synthetic triglyceride, or may be a mixture of several triglycerides. Fats isolated from natural sources usually are available only as mixtures of triglycerides. Such natural mixtures are suitable for the preparation of dry lipid mixtures, provided that the melting characteristics of the mixture are such that they exhibit a solid or liquid crystal phase at about 25° C.

Examples of solid fats suitable for the preparation of dry lipid mixtures of the present technology are triglycerides composed of natural, even-numbered and unbranched fatty acids with chain lengths in the C10-C18 range, or microcrystalline glycerol triesters of saturated, even-numbered and unbranched fatty acids of natural origin such as tricaprin, trilaurin, trimyristin, tripalmitin, and tristearin.

The content of solid triglycerides in the final dry lipid mixture is in the range of between about 20% and about 75% of the total solid weight of the mixture, or between about 25% and about 50% of the total solid weight of the mixture, or between about 30% and about 45% of the total solid weight of the mixture.

Phospholipids which may enter into the composition of the dry lipid mixture of the present technology include, but are not limited, natural phospholipids, such as: soybean lecithin, egg lecithin, phosphatidylglycerol, phosphatidylinositol, phosphatidylethanolamine, phosphatidic acid, sphingomyelin, diphosphatidylglycerol, phosphatidylserine, phosphatidylcholine, cardiolipin; synthetic phospholipids, such as dimyristoylphosphatidylcholine, dimyristoyl-phosphatidylglycerol, distearoylphosphatidylglycerol, dipalmitoylphosphatidylcholine; and hydrogenated or partially hydrogenated lecithins and phospholipids.

The phospholipid component may be either saturated or unsaturated and may have a gel to fluid phase transition temperature either above or below about 25° C. Egg or soy phosphatidylcholines (egg or soy PC) are examples of phospholipids with transition temperatures well below room temperature. Dimyristoyl phosphatidylcholine (DMPC) has a transition temperature slightly below room temperature. Dipalmitoyl and distearoyl phosphatidylcholines (DPPC and DSPC) are examples of phospholipids with transition temperatures well above room temperature, and, in fact, even above physiological temperature (about 37° C.). Acceptable dry lipid mixtures may be made with these and many other phospholipids.

Dry lipid mixtures may be prepared with molar ratios of phospholipid to total lipid in the range of between about 0.1 and about 0.75 (about 10 to 75 mol %), or between about 0.1 and about 0.5 (about 10 to 50 mol %). The molar ratio of phospholipid to total lipid typically may be in the range of between about 0.1:1 and about 2:1, or between about 0.1:1 and about 1:1, or between about 0.2:1 and about 0.9:1, or between about 0.2:1 and about 0.8:1, or between about 0.25:1 and about 0.6:1. On a weight basis, the ratio of phospholipid to total lipid is between about 0.1:1 and about 2:1, or between about 0.2:1 and about 1:1, or between about 0.4:1 and about 1.5:1, or between about 0.5:1 and about 1.25:1. The content of phospholipids in the final dry solid lipid mixture is in the range of between about 2% and about 40% of the total solid weight of the mixture, or between about 5% and about 35% of total solid weight of the mixture, or between about 10% and about 30% of total solid weight of the mixture.

The dry solid lipid mixture of the present technology may comprise one or more additional antioxidants. Antioxidants lessen the formation of oxidative degradation products, such as peroxides, from the unsaturated lipids, or other components. A non-limiting example of such a preferred antioxidant is α-tocopherol, or its derivatives (such as tocopherol succinate), which are members of the Vitamin E family. Many other antioxidants which are known in the art as safe for human consumption may be used, such as butylated hydroxytoluene (BHT). The content of the antioxidant in the final dry solid lipid mixture is commonly in the range of between about 0.01% and about 5% of the total solid weight of the mixture, or between about 0.1 and about 1% of the total solid weight of the mixture. Dry solid lipid mixtures may further comprise a cryoprotectant material as known in the art, such as a sugar or an amino compound, to preserve the formulation during freeze-drying or spray-drying processes used in the preparation of the dry solid CoQ10-lipid mixtures.

Examples of cryoprotectants that may be useful in the present technology include, but are not limited to: glucose, sucrose, lactose, maltose, and trehalose; polysaccharides, such as dextrose, dextrins, and cyclodextrins; and non-natural polymers, such as polyvinylpyrrolidone (PVP). Other types of cryoprotectants may also be used, including amino acids, as disclosed in U.S. Pat. No. 5,472,706, incorporated herein by reference. Examples of range of cryoprotectant to total solids in the dry solid lipid mixtures include between about 0.1% and about 50% (w/w), or between about 20% and about 40% may be used.

The dry solid lipid mixtures of the present technology may further comprise any suitable nontoxic carrier or diluent powder, known in the art, to serve as a free-flow imparting agent. Common examples of such additives are silicon dioxide, starch, lactose, sucrose, sorbitol, talc, stearic acid, magnesium stearate, and dicalcium phosphate. When the mixture is formulated into a tablet or pill, the tablet or pill can be coated or otherwise compounded with pharmaceutically acceptable materials known in the art to provide a dosage form affording prolonged action or sustained release. The dry solid lipid mixtures may also be prepared in gelatin capsules. But, theses mixtures may simply be mixed with any sort of animal feed product by co-milling or other mixing process.

According to a further embodiment, the dry solid lipid mixtures are further mixed with fumed silica such as CAB-0-SIL® (Cabot Corp., Ill., US), which is fumed silicon dioxide. This compound is a powdery material with extremely small particle size and enormous surface area. Fumed silica can act as a dry lubricant, promoting the free flow of the powdery mixture and preventing the mixture from caking or lumping. The free-flow, anti-caking and anti-clogging characteristics of this compound are the result of several actions. For example, the submicroscopic size of the silica aggregates permits them to move easily between the larger particles of the other dry agents, and, in most cases, fumed silica probably forms a coating on the powder particles. The fumed silica layer also decreases bulk tensile strength and shear strength, while neutralizing the electro-static charge on the particles.

After blending with the other powders, fumed silica adsorbs some or all the moisture which may be present in or on the product particles. The fumed silica aggregates, therefore, prevent other particles from contacting each other and, in turn, from forming the nuclei that would otherwise lead to the formation of larger lumps and cakes. This spacing and lubricating action helps to keep materials moving through apertures, such as process equipment valves, spray heads, storage bin openings, bag and drum spouts and aerosol nozzle orifices.

Most powdered materials can be kept free flowing by adding a concentration of fumed silica in the final product range between about 0.5% and about 50% (total solid weight). The optimum concentration can be determined by working up or down in small steps. The weight percent of fumed silica in the final product will be in the range of between about 1% and about 40% (total solid weight). Even powders which have already become caked can usually be rendered free flowing by blending them in fumed silica (about 2% of the total solid weight, or less). The tremendous surface area of fumed silica is the reason very small amounts can provide effective action.

Products which cannot be processed beyond a sticky or tacky powder can be made free flowing by adding the proper level of fumed silica as a final finishing step. Fumed silica can also be used to promote free flow in spray-dried or freeze-dried products. In some cases it can be introduced into the original emulsion, suspension or solution, or blended in later. Fumed silica has also been used to coat powdered and pelletized products to prevent them from caking later. The content of silicon dioxide in the final dry solid lipid mixture is in the range of between about 5% and about 40% of the total solid weight of the mixture. The dry target component-lipid mixtures of the present technology may be prepared by different methods as described in the following non-limiting examples appearing below.

EXAMPLE

The examples below are given so as to illustrate the practice of various embodiments of the present disclosure. They are not intended to limit or define the entire scope of this disclosure. It should be appreciated that the disclosure is not limited to the particular embodiments described and illustrated herein but includes all modifications and variations falling within the scope of the disclosure as defined in the appended embodiments.

Any element of any embodiment may be used in any embodiment. Although the technology has been described with reference to specific embodiments, it will be understood by those skilled in the art that various changes may be made and equivalents may be substituted for elements thereof without departing from the true spirit and scope of the invention. In addition, modifications may be made without departing from the essential teachings of the invention.

Identification of equivalent compositions, methods and kits are well within the skill of the ordinary practitioner and would require no more than routine experimentation, in light of the teachings of the present disclosure. Practice of the disclosure will be still more fully understood from the following examples, which are presented herein for illustration only and should not be construed as limiting the disclosure in any way.

Example 1: *Asparagopsis* Quantity Calculation for a Given Reduction in Methane Production Table 1 shows the *Asparagopsis* quantity calculation for a given reduction in methane production in dairy cattle based on normal dietary requirements and measured bromoform level in the algal biomass supplement.

TABLE 1

| Asparagopsis quantity calculation | Value |
|---|---|
| Feed intake (kg/day) | 27.70 |
| NDF concentration (%) | 30.10% |
| NDF intake per day (kg/day) | 8.34 |
| y-intercept-Methane intensity (g of CH4/kg of milk, at zero bromoform intake) | 9.73 |
| Slope-Reduction in methane intensity (g CH4/kg milk) per normalized unit bromoform intake (mg/kg of NDF) | −0.049 |
| Desired % reduction in CH4 | −80.00% |
| Desired absolute reduction in CH4 (g/kg milk) | −7.784 |
| Normalized bromoform required (mg/kg of NDF) | 157.89 |
| Bromoform required (mg/day) | 1316.44 |
| Dried AT Bromoform Concentration (µg/g) | 35 |
| Asparagopsis per cow per day (g)-DMI basis | 37.61 |
| Seaweed % DMI | 95% |
| Asparagopsis per cow per day (g)-as-fed basis | 39.59 |

Examples 2a,b a) Iodine Exposure Based on a 120 g Daily Dose of Supplement

Table 2a shows the iodine exposure based on a 120 g daily dose of supplement comprising *Asparagopsis taxiformis brominata* comprising a total iodine content of 1000 ppm (0.1%) and a total DMI of 20 kg.

TABLE 2a

| | |
|---|---|
| Amount of Algae | 120 g |
| Iodine Content | 0.1% |
| Total Iodine | 120 mg |
| DMI per day | 20 Kg |
| Iodine per Kg DMI per Day | 6 mg/Kg-Day | b) Calculated Supplementation Rates for Animals Under Different Conditions

The methods of supplementation rate determination of the present technology, as illustrated in FIGS. 12 and 13 can be used in a variety of circumstances, taking into account the bromoform content of the supplement and the type of diet an animal is receiving. For example, in table 2b below, illustrative supplementation rates of an algal biomass derived supplement comprising 35,000 µg/g (35 mg/g or 3.5% by dry weight of bromoform are given for dairy cows on feed, dairy cows on pasture, beef steers on pasture, beef steers on a transitioning diet, and beef steers on a finishing diet.

TABLE 2b

| Animal/Diet | NDF intake (kg/day) | Supplementation rate of algal biomass (3.5% bromoform) (g/day) |
|---|---|---|
| Dairy Cow on Feed | 7.7 | 40 |
| Dairy Cow on Pasture | 12.1* | 63 |
| Beef Steer on Pasture | 3.1 | 16 |
| Beef Steer on Transition | 2.8 | 15 |
| Beef Steer on Finishing | 2.0 | 11 |

*Approximate value, may increase or decrease based on dry matter intake (DMI) and Neutral Detergent Fiber (NDF)

Example 3: Encapsulation: Preparation of Dry Bromoform-Lipid Mixture by Freeze-Drying from an Aqueous Dispersion This example illustrates the preparation of a dry bromoform-lipid mixture by freeze-drying from an aqueous dispersion according to one embodiment of the present technology. The final dry composition of the formulation comprises:

Bromoform: 11.7% w/w
Tricaprin: 33.7% w/w
Lecithin: 16.8% w/w
Tocopherol succinate: 0.4% w/w
Sucrose: 23.9% w/w
Silicon dioxide: 13.5% w/w.

Bromoform is obtained from Sigma-Aldrich, Inc. D-α tocopherol succinate is purchased from Merck (Germany). Lecithin is obtained from Lipoid KG (Germany). Tricaprin is obtained from Hulls (Germany). CAB-O-SIL is obtained from Cabot Corp. bromoform is dissolved together with the lipid agents (phospholipids, tocopherol succinate and solid triglycerides) in dichloromethane. The solvent is evaporated until complete dryness, and the dry solid lipid mixture is then hydrated with the aqueous phase by mechanical shaking. The resultant lipid dispersion is consequently homogenized by high-pressure homogenization (800 bar) using an EMULSIFLEX™ C-30 high pressure homogenizer (Avestin Inc., Canada) to reduce the particle size to the submicron range. To the resultant dry bromoform-lipid preparation, the cryoprotectant, sucrose (from a 40% w/w water solution), and the free-flowing imparting agent, CAB-0-SIL fumed silicon dioxide (from a 5% w/w suspension in water), are added and the formulation is then freeze-dried using a Christ lyophilizer (Germany). The weight ratio of phospholipids to total lipids is 0.33:1.

Example 4: Bromoform-Iodine Ratio Variation from Different AT Compositions

Table 3 shows some possible bromoform-iodine ration variation from different AT compositions from seedstock harvested from various locations and grown at different light intensities and photoperiods. All but Nos. 9 and 10 are tetrasporophytes.

TABLE 3

| Number | Location | % HCBr$_3$ | % Iodine | Iodine: HCBr$_3$ Ratio | HCBr$_3$: Iodine Ratio |
|---|---|---|---|---|---|
| 1 | MB-JES012 | 0.803 | 0.0339 | 0.0422 | 23.70 |
| 2 | CI-JES002 | 1.620 | 0.0372 | 0.0230 | 43.50 |

TABLE 3-continued

| Number | Location | % HCBr₃ | % Iodine | Iodine:HCBr₃ Ratio | HCBr₃:Iodine Ratio |
|---|---|---|---|---|---|
| 3 | Pier (high light)-JES016 | 0.521 | 0.0239 | 0.0459 | 21.80 |
| 4 | Pier (low light)-JES015 | 0.177 | 0.0967 | 0.5463 | 1.80 |
| 5 | Birch-JES019 | 1.060 | 0.0464 | 0.0438 | 22.80 |
| 6 | SIO-13B2 | 0.263 | 0.0868 | 0.3300 | 3.00 |
| 7 | SC-S-112 | 0.406 | 0.0383 | 0.0943 | 10.60 |
| 8 | SC-S-JES014 | 0.641 | 0.0378 | 0.0590 | 17.00 |
| 9 | MB Gametophytes | 0.396 | 0.0456 | 0.1152 | 8.70 |
| 10 | Chunky boy Gametophytes | 1.940 | 0.5977 | 0.3081 | 3.20 |
| 11 | Light Experiment | 0.615 | 0.0227 | 0.0369 | 27.10 |
| 12 | Light Experiment | 0.604 | 0.0320 | 0.0530 | 18.90 |
| 13 | Light Experiment | 0.672 | 0.0245 | 0.0365 | 27.40 |
| 14 | Light Experiment | 0.885 | 0.0580 | 0.0655 | 15.30 |
| 15 | Light Experiment | 1.850 | 0.0326 | 0.0176 | 56.70 |
| 16 | Light Experiment | 1.260 | 0.0156 | 0.0124 | 80.80 |
| 17 | Light Experiment | 1.040 | 0.0282 | 0.0271 | 36.90 |
| 18 | Light Experiment | 1.190 | 0.0142 | 0.0119 | 83.80 |

Table 4 shows the typical gametophyte Heavy Metal and Iodine Analysis and natural variation.

TABLE 4

Gametophyte Component Analysis

| Wild Harvested Gametophytes from the Azores | | | Wild Harvested Gametophytes from the Azores and Australia | | |
|---|---|---|---|---|---|
| Heavy Metals | Result | Unit | Heavy Metals | Result | Unit |
| Aluminum | 600.5 | ppm | Aluminum | 4093.3 | ppm |
| Antimony | <5 | ppm | Antimony | <5 | ppm |
| Arsenic | 12.8 | ppm | Arsenic | 14.1 | ppm |
| Barium | 4.7 | ppm | Barium | 10.7 | ppm |
| Boron | 108.4 | ppm | Boron | 108.6 | ppm |
| Cadmium | 0.5 | ppm | Cadmium | 0.5 | ppm |
| Calcium | 20242.8 | ppm | Calcium | 24479.5 | ppm |
| Chromium | 20.7 | ppm | Chromium | 84.2 | ppm |
| Cobalt | <1 | ppm | Cobalt | 3.5 | ppm |
| Copper | 2.6 | ppm | Copper | 6.2 | ppm |
| Iodine | 9733 | ppm | * Iodine | 2730 | ppm |
| Iron | 1301.8 | ppm | Iron | 5251 | ppm |
| Lead | <2.5 | ppm | Lead | <2.5 | ppm |
| Magnesium | 9696.4 | ppm | Magnesium | 10121.2 | ppm |
| Manganese | 31.2 | ppm | Manganese | 99.5 | ppm |
| Mercury | <10 | ppm | Mercury | <10 | ppm |
| Molybdenum | 1.9 | ppm | Molybdenum | 2.3 | ppm |
| Phosphorus | 1835.4 | ppm | Phosphorus | 1693.8 | ppm |
| Potassium | 17980.3 | ppm | Potassium | 16041.9 | ppm |
| Selenium | 0.2 | ppm | Selenium | 0.3 | ppm |
| Sodium | 84741.8 | ppm | Sodium | 71571 | ppm |
| Sulfur | 31889.7 | ppm | Sulfur | 30656.5 | ppm |
| Thallium | <10 | ppm | Thallium | <10 | ppm |
| Zinc | 8.6 | ppm | Zinc | 14.4 | ppm |
| Bromoform | 18600 | ppm | Bromoform | 4250 | ppm |

Heavy metal analysis performed by Cumberland Valley Analytical Services, Waynesboro, PA 17268
Bromoform analysis performed by Bigelow Laboratory for Ocean Sciences, East Boothbay, ME 04544
Iodine analysis for the Azores batch was performed by Bigelow Laboratory for Ocean Sciences, East Boothbay, ME 04544
Iodine analysis for the Azores-Australia mix batch was performed by Cumberland Valley Analytical Services, Waynesboro, PA 17268

TABLE 5

Intake limits of various minerals for dairy cattle, based on feed composition and total exposure.

| | Tolerability Limits | |
|---|---|---|
| | Maximum Allowable Component Intake Limit per Daily kg of DM Consumption mg/kg DMI | Intake for a Cow Consuming 20.14 kg DM/day mg/day |
| Aluminum | 1000 | 20140 |
| Antimony | | |
| Arsenic | 30 | 604 |
| Barium | | |
| Boron | 150 | 3021 |
| Cadmium | 10 | 201 |
| Calcium | 15000 | 302100 |
| Chromium | 100 | 2014 |
| Cobalt | 25 | 504 |
| Copper | 40 | 806 |
| Iodine | 50 | 1007 |
| Iron | 500 | 10070 |
| Lead | 100 | 2014 |
| Magnesium | 6000 | 120840 |
| Manganese | 2000 | 40280 |
| Mercury | 2 | 40 |
| Molybdenum | 5 | 101 |
| Phosphorous | 7000 | 140980 |
| Potassium | 20000 | 402800 |
| Selenium | 5 | 101 |
| Sodium | 84742 | 1706704 |
| Sulfur | 3000 | 60420 |
| Thalium | | |
| Zinc | 500 | 10070 |

TABLE 6

Calculated mineral exposures from a 120 g/day dose of a Gametophyte based algal supplement showing excessive iodine exposure.

Typical Gametophyte Composition In Use Now

| Azores and Australia Mix | Mineral content of seaweed mg/kg mg/kg | Daily mg mineral exposure at 120 g/day seaweed Intake mg |
|---|---|---|
| Aluminum | 4093 | 491.20 |
| Antimony | <5 | <0.6 |
| Arsenic | 14 | 1.69 |
| Barium | 11 | 1.28 |
| Boron | 109 | 13.03 |
| Cadmium | 1 | 0.06 |
| Calcium | 24480 | 2937.54 |
| Chromium | 84 | 10.10 |
| Cobalt | 4 | 0.42 |
| Copper | 6 | 0.74 |
| Iodine | 2730 | 327.60 |
| Iron | 5251 | 630.12 |
| Lead | <2.5 | <0.3 |
| Magnesium | 10121 | 1214.54 |
| Manganese | 100 | 11.94 |
| Mercury | <10.0 | <1.2 |
| Molybdenum | 2 | 0.28 |
| Phosphorous | 1694 | 203.26 |
| Potassium | 16042 | 1925.03 |
| Selenium | 0.30 | 0.04 |
| Sodium | 71571 | 8588.52 |
| Sulfur | 30657 | 3678.78 |
| Thalium | <10.0 | <1.2 |
| Zinc | 14 | 1.73 |

53

TABLE 7

Typical Brominata analysis showing much
lower iodine and aluminum content.
Brominata Component Analysis

| Element | Amount | Unit |
|---|---|---|
| Aluminum | 13.3 | ppm |
| Antimony | <5 | ppm |
| Arsenic | <2.5 | ppm |
| Barium | 0.6 | ppm |
| Boron | 239 | ppm |
| Cadmium | 0.05 | ppm |
| Calcium | 3666.2 | ppm |
| Chromium | 1.1 | ppm |
| Cobalt | <1 | ppm |
| Copper | 8.6 | ppm |
| Iodine | 460 | ppm |
| Iron | 1972 | ppm |
| Lead | <2.5 | ppm |
| Magnesium | 6572.8 | ppm |
| Manganese | 124.7 | ppm |
| Mercury | <10 | ppm |
| Molybdenum | 0.9 | ppm |
| Phosphorus | 2716.1 | ppm |
| Potassium | 15067.7 | ppm |
| Selenium | 0.1 | ppm |
| Sodium | 33239.6 | ppm |
| Sulfur | 26158 | ppm |
| Thallium | <10 | ppm |
| Zinc | 10.8 | ppm |

TABLE 8

Example of two commercially blended mineral supplements with
calculated exposures at recommended supplementation rates.

| | Supplements | | | |
|---|---|---|---|---|
| | Mineral Content of Supplement for Lactating Cow | | Mineral Content of Supplement for Dry Cow | |
| | mg/kg | Mineral Intake at 220 g/day Supplementation mg/day | Mineral Content of Supplement mg/kg | Mineral Intake at 454 g/day Supplementation mg/day |
| Aluminum | | | | |
| Antimony | | | | |
| Arsenic | | | | |
| Barium | | | | |
| Boron | | | | |
| Cadmium | | | | |
| Calcium | 214369 | 128621 | 239808 | 143884.8 |
| Chromium | | | | |
| Cobalt | 20.4 | 12 | 4 | 2.4 |
| Copper | 605 | 363 | 369 | 221.4 |
| Iodine | 71.6 | 43 | 25.9 | 15.54 |
| Iron | 87.7 | 53 | 40.5 | 24.3 |
| Lead | | | | |
| Magnesium | 59824 | 35895 | 59976 | 35985.6 |
| Manganese | 1004 | 602 | 214 | 128.4 |
| Mercury | | | | |
| Molybdenum | | | | |
| Phosphorus | 3.8 | 2.28 | 1.4 | 0.84 |
| Potassium | 45563 | 27338 | 7 | 4.2 |
| Selenium | 29.7 | 17.82 | 9.1 | 5.46 |
| Sodium | 59632 | 35779 | 154 | 92.4 |
| Sulfur | 19793 | 11876 | 45027 | 27016.2 |
| Thallium | | | | |
| Zinc | 3546 | 2128 | 1576 | 945.6 |

54

All references cited in this specification, and their references, are incorporated by reference herein in their entirety where appropriate for teachings of additional or alternative details, features, and/or technical background.

While the disclosure has been particularly shown and described with reference to particular embodiments, it will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

The invention claimed is:

1. A composition comprising algae biomass comprising greater than about 5 (mg/g) w/w dried material of bromoform, wherein the algae biomass is *Asparagopsis taxiformis* tetrasporophyte.

2. The composition of claim 1, comprising greater than about 10 (mg/g) w/w dried material of bromoform.

3. The composition of claim 1, having a bromoform/iodine ratio equal or greater than about 5 (µg/g)/ppm dried material.

4. The composition of claim 1, having a bromoform/iodine ratio equal or greater than about 5 (µg/g)/ppm dried material.

5. The composition of claim 1, having a bromoform/iodine ratio equal or greater than about 2 (µg/g)/ppm dried material.

6. The composition of claim 1, comprising greater than about 9 (mg/g) w/w dried material of bromoform, having a bromoform/iodine ratio equal or greater than about 5 (µg/g)/ppm dried material.

7. The composition of claim 1, comprising greater than about 9 (mg/g) w/w dried material of bromoform, having a bromoform/iodine ratio equal or greater than about 2 (µg/g)/ppm dried material.

8. A composition comprising algae biomass wherein the composition comprises less than 0.145 w/w % dry weight iodine, wherein the algae biomass is *Asparagopsis taxiformis* tetrasporophyte.

9. A composition comprising algae biomass wherein the composition comprises more than 1.8 w/w % dry weight of bromoform, wherein the algae biomass is *Asparagopsis taxiformis* tetrasporophyte.

10. The composition of claim 9, wherein the biomass is a non-filamentous tetrasporophyte algae biomass.

11. The composition of claim 1, wherein the biomass is a non-filamentous tetrasporophyte algae biomass.

12. The composition of claim 8, wherein the biomass is a non-filamentous tetrasporophyte algae biomass.

* * * * *